United States Patent
Fueyo et al.

(10) Patent No.: US 8,548,823 B2
(45) Date of Patent: *Oct. 1, 2013

(54) AUTOMATICALLY DETERMINING IDEAL TREATMENT PLANS FOR COMPLEX NEUROPSYCHIATRIC CONDITIONS

(75) Inventors: Joanna Lynn Fueyo, Brighton, MA (US); Robert Lee Angell, Salt Lake City, UT (US); Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 1139 days.

This patent is subject to a terminal disclaimer.

(21) Appl. No.: 12/169,329

(22) Filed: Jul. 8, 2008

(65) Prior Publication Data

US 2010/0010831 A1    Jan. 14, 2010

(51) Int. Cl.
G06Q 10/00    (2012.01)
G06F 19/00    (2011.01)

(52) U.S. Cl.
USPC .................................................. 705/2; 705/3

(58) Field of Classification Search
USPC ....................................................... 705/2–3
See application file for complete search history.

(56) References Cited

U.S. PATENT DOCUMENTS

| | | | |
|---|---|---|---|
| 5,832,450 A | 11/1998 | Myers et al. | |
| 5,845,255 A | 12/1998 | Mayaud | |
| 5,873,823 A | 2/1999 | Eidelberg et al. | |
| 7,051,022 B1 | 5/2006 | Faisal | |
| 7,244,231 B2 | 7/2007 | Dewing et al. | |
| 7,269,516 B2 | 9/2007 | Brunner et al. | |
| 7,428,323 B2 | 9/2008 | Hillman | |
| 7,599,995 B1 | 10/2009 | Fernandez et al. | |
| 7,844,560 B2 | 11/2010 | Krishnan et al. | |

(Continued)

FOREIGN PATENT DOCUMENTS

| | | |
|---|---|---|
| JP | 2005-237441 A | 9/2005 |
| JP | 2006-204641 A | 8/2006 |
| WO | 2007019504 | 2/2007 |
| WO | 2007/063656 A1 | 6/2007 |

OTHER PUBLICATIONS

Barrett (Barrett, K.F. et al. "Regional CBF in chronic stable TBI treated with hyperbaric oxygen." Undersea & Hyperbaric Medicine; Winter 2004; 31, 4; ProQuest Health and Medical Complete. p. 395).*
U.S. Appl. No. 12/141,316, filed Jun. 18, 2008, Fueyo et al.

(Continued)

*Primary Examiner* — Michelle Le
(74) *Attorney, Agent, or Firm* — Yee & Associates, P.C.; John R. Pivnichny

(57) ABSTRACT

A computer implemented method, apparatus, and computer program product for modifying neuropsychiatric treatment plans based on efficacy of treatment. A current treatment plan comprising a first set of therapies to treat a set of neuropsychiatric conditions and portions of the medical literature associated with the set of neuropsychiatric conditions is retrieved. A set of brain scans of the patient is analyzed to determine a set of changes over time associated with the set of neuropsychiatric conditions. The portions of the medical literature and the set of changes are analyzed to determine a patient rate of response to the treatment plan. If the patient rate of response falls below a threshold expected rate, a set of alternative treatments for the patient is identified. A modified treatment plan is generated using the set of alternative treatments.

25 Claims, 9 Drawing Sheets

(56) References Cited

U.S. PATENT DOCUMENTS

| | | | |
|---|---|---|---|
| 7,912,528 B2 | 3/2011 | Krishnan et al. | |
| 7,929,737 B2 | 4/2011 | Sirohey et al. | |
| 7,996,242 B2 | 8/2011 | Fueyo et al. | |
| 8,064,986 B2 | 11/2011 | Profio et al. | |
| 8,126,112 B2 | 2/2012 | Massie et al. | |
| 8,126,228 B2 | 2/2012 | Fueyo et al. | |
| 8,199,982 B2 | 6/2012 | Fueyo et al. | |
| 8,280,482 B2 | 10/2012 | Rusinek et al. | |
| 8,388,529 B2 | 3/2013 | Fueyo et al. | |
| 2003/0100998 A2 | 5/2003 | Brunner et al. | |
| 2004/0093331 A1 | 5/2004 | Garner et al. | |
| 2005/0020903 A1 | 1/2005 | Krishnan et al. | |
| 2005/0038678 A1 | 2/2005 | Qian et al. | |
| 2005/0043965 A1* | 2/2005 | Heller et al. | 705/2 |
| 2005/0091191 A1 | 4/2005 | Miller et al. | |
| 2005/0107682 A1 | 5/2005 | Rao et al. | |
| 2005/0215889 A1 | 9/2005 | Patterson | |
| 2005/0244036 A1 | 11/2005 | Rusinek | |
| 2006/0120584 A1 | 6/2006 | Hillman | |
| 2006/0270926 A1 | 11/2006 | Hu et al. | |
| 2007/0129627 A1 | 6/2007 | Profio et al. | |
| 2007/0276777 A1* | 11/2007 | Krishnan et al. | 706/46 |
| 2008/0077001 A1 | 3/2008 | Ruscio et al. | |
| 2009/0006061 A1 | 1/2009 | Thukral et al. | |
| 2009/0124882 A1 | 5/2009 | Massie et al. | |
| 2009/0149898 A1 | 6/2009 | Hulvershorn et al. | |
| 2009/0316968 A1 | 12/2009 | Fueyo et al. | |
| 2009/0316969 A1 | 12/2009 | Fueyo et al. | |
| 2010/0010316 A1 | 1/2010 | Fueyo et al. | |
| 2010/0010363 A1 | 1/2010 | Fueyo et al. | |
| 2010/0010827 A1 | 1/2010 | Fueyo et al. | |
| 2012/0207362 A1 | 8/2012 | Fueyo et al. | |

OTHER PUBLICATIONS

U.S. Appl. No. 12/169,339, filed Jul. 8, 2008, Fueyo et al.
U.S. Appl. No. 12/169,402, filed Jul. 8, 2008, Fueyo et al.
U.S. Appl. No. 12/141,322, filed Jun. 18, 2008, Fueyo et al.
U.S. Appl. No. 12/169,350, filed Jul. 8, 2008, Fueyo et al.
USPTO office action for U.S. Appl. No. 12/169,402 dated Oct. 28, 2010.
USPTO Notice of allowance for U.S. Appl. No. 12/169,402 dated Apr. 6, 2011.
USPTO Office action dated Jul. 7, 2011 for U.S. Appl. No. 12/141,322.
Office Action issued on Sep. 22, 2011 for U.S. Appl. No. 12/141,316, 26 pages.
Notice of Allowance issued on Feb. 9, 2012 for U.S. Appl. No. 12/141,316, 7 pages.
Notice of Allowance issued on Oct. 24, 2011 for U.S. Appl. No. 12/141,322, 7 pages.
Office Action issued on Jan. 20, 2012 for U.S. Appl. No. 12/169,350, 28 pages.
Office Action issued on Jul. 17, 2012 for U.S. Appl. No. 12/169,350, 34 pages.
European Search Report, dated Mar. 27, 2009, regarding Application No. EP08167756.9, 10 pages.
Japanese Patent Office Notification of Reasons for Rejection, dated Aug. 11, 2009, regarding Application No. JP2008-279718, 7 pages.
Aberle et al, Database Design and Implementation for Quantitative Image Analysis Research, IEEE Transactions on Information Technology in Biomedicine, vol. 9, No. 1, Mar. 2005, pp. 99-108.
Rahman et al, "Medical Image Retrieval and Registration: Towards Computer Assisted Diagnostic Approach," Proceedings of the IDEAS Workshop on Medical Information Systems: The Digital Hospital (IDEAS-DH'04), Sep. 2004, pp. 78-89.
Notice of Allowance, dated Nov. 2, 2012, regarding USPTO U.S. Appl. No. 12/169,339, 9 pages.
Final Office Action, dated Feb. 8, 2013, regarding USPTO U.S. Appl. No. 12/169,350, 34 pages.

* cited by examiner

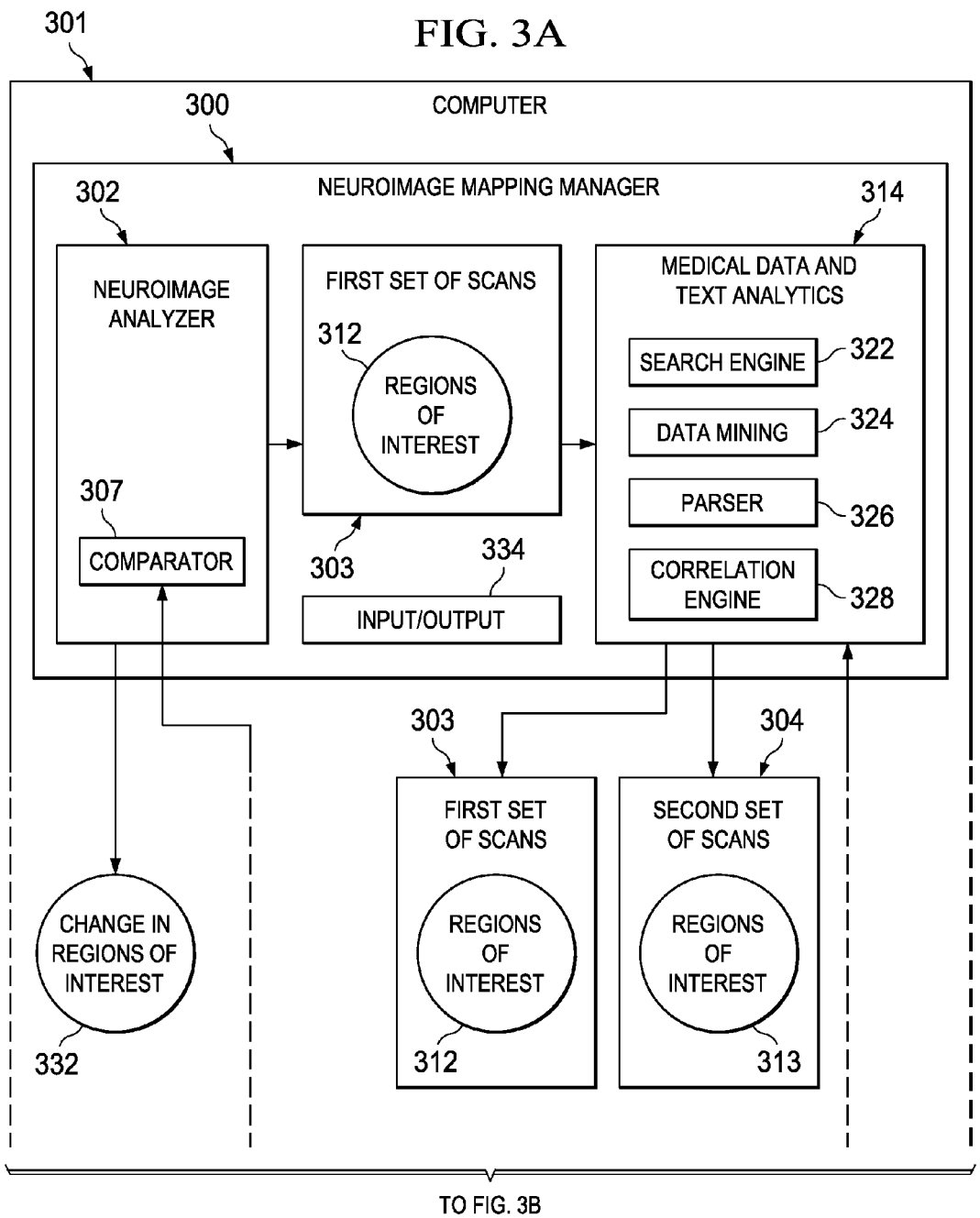

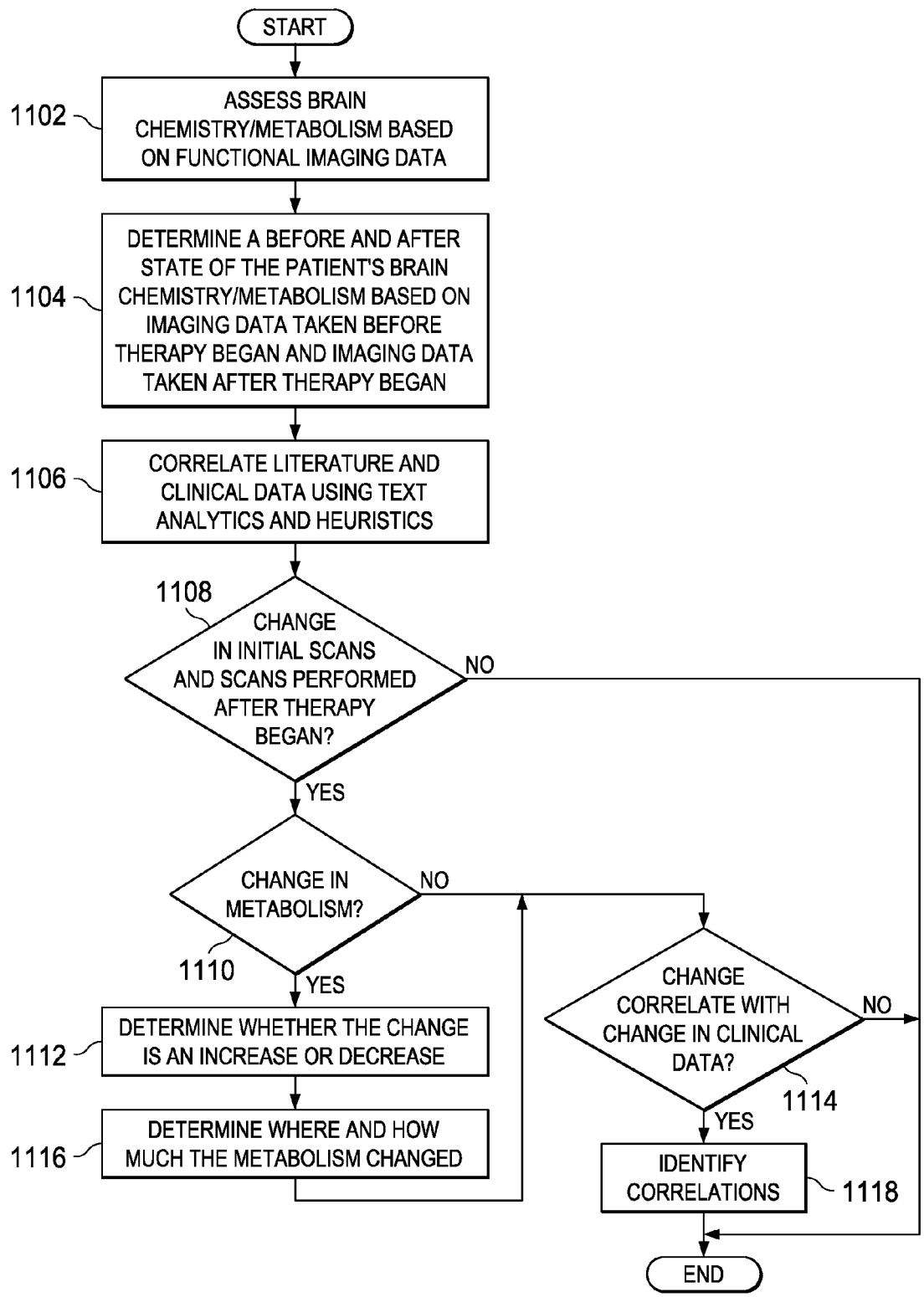

AUTOMATICALLY DETERMINING IDEAL TREATMENT PLANS FOR COMPLEX NEUROPSYCHIATRIC CONDITIONS

BACKGROUND OF THE INVENTION

1. Field of the Invention

The present invention is related generally to a data processing system and in particular to a method and apparatus for developing treatment plans. More particularly, the present invention is directed to a computer implemented method, apparatus, and computer usable program code for modifying neuropsychiatric treatment plans based on efficacy of treatment.

2. Description of the Related Art

Neuropsychiatric conditions typically have neurological features associated with disorders of the nervous system, as well as psychiatric features. Neuropsychiatric conditions may be treated using a variety of therapies, such as talk therapy, behavioral therapy, chemical therapy, and/or mechanical therapy. Chemical therapy refers to pharmacotherapy, such as, the utilization of drugs. Mechanical therapy includes electroconvulsive therapies (ECT). These therapies may be used separately or may be used in combination to treat patients.

However, some patients may not receive the most effective treatments available due to difficulties in accurately diagnosing patients with neuropsychiatric conditions. In addition, patients that are accurately diagnosed may suffer from the negative side effects of effective therapies and/or trails of ineffective therapies. Furthermore, some patients may suffer for years as a result of poorly understood disease phenotype, particularly in cases involving the presentation of complex cases and/or multiple conditions in a single patient. In addition, when a disease is developing in a patient and the patient has not had a sufficient number of "episodes" for diagnosis or has only manifested a few early stage symptoms, it may be difficult or impossible to clearly and rapidly delineate a differential diagnosis.

BRIEF SUMMARY OF THE INVENTION

According to one embodiment of the present invention, a computer implemented method, apparatus, and computer program product is provided for modifying neuropsychiatric treatment plans based on efficacy of treatment.

A treatment plan generator retrieves a current treatment plan for a patient. The current treatment plan comprises a first set of therapies to treat a set of neuropsychiatric conditions and portions of the medical literature associated with the first set of therapies. A neuroimage analyzer analyzes a set of brain scans of the patient to determine a set of changes over time associated with the set of neuropsychiatric conditions. The set of scans comprises a first set of scans taken at a first time and a second set of scans taken at a second time. The treatment plan generator analyzes the portions of the medical literature associated with the set of neuropsychiatric conditions and the set of changes associated with the neuropsychiatric conditions to determine a patient rate of response to the treatment plan. In response to the patient rate of response to the treatment plan falling below a threshold expected rate, the treatment plan generator identifies a set of alternative treatments for the patient and generates a modified treatment plan using set of alternative treatments.

In one embodiment, the first set of scans taken at the first time are generated prior to beginning implementation of a therapy in the set of therapies to treat the patient and wherein the second set of scans taken at the second time are generated a given period of time after beginning implementation of the therapy in the set of therapies.

In another embodiment, the treatment plan generator presents a result of analyzing portions of the medical literature associated with the set of neuropsychiatric conditions, the set of changes associated with the neuropsychiatric conditions, and the treatments in the current treatment plan to a user. The result comprises the current treatment plan and the patient rate of response associated with each neuropsychiatric condition in the set of neuropsychiatric conditions. In response to receiving a selection of at least one of neuropsychiatric conditions from the set of neuropsychiatric conditions to form a subset of selected neuropsychiatric conditions, the treatment plan generator generates the set of alternative treatments.

In yet another embodiment, the set of neuropsychiatric conditions associated with the patient are identified in a current set of diagnoses. The treatment plan generator receives an updated set of diagnoses for the patient, wherein the updated set of diagnoses identifies a different set of neuropsychiatric conditions than the current set of diagnoses. The treatment plan generator analyzes portions of the medical literature associated with the different set of neuropsychiatric conditions to identify a set of recommended treatments for the different set of neuropsychiatric conditions. The treatment plan generator generates the modified treatment plan using the set of recommended treatments for the different set of neuropsychiatric conditions.

In yet another embodiment, the neuroimage analyzer identifies a first set of regions of interest in the first set of scans and a second set of regions of interest in the second set of scans and compares the first set of regions of interest with the second set of regions of interest to identify a set of changes in the regions of interest occurring over time. The rate of response is determined based on the set of changes. A medical data and text analytics component identifies portions of the medical literature associated with the set of changes. The treatment plan generator generates the modified treatment plan. The modified treatment plan comprises a set of links to the portions of the relevant medical literature associated with the set of changes in the regions of interest.

In another embodiment, the treatment plan generator identifies negative drug interactions, side effects, allergic reactions, and negative effects on pre-existing conditions of the patient associated with the set of alternative treatments for the given neuropsychiatric condition. The treatment plan generator presents the modified treatment plan with the negative drug interactions, side effects, allergic reactions, and negative effects on pre-existing conditions of the patient associated with the set of alternative treatments for the given neuropsychiatric condition.

In one embodiment, the neuroimage analyzer may also generate quantitative information describing a set of changes associated with the neuropsychiatric conditions of the patient occurring over time, wherein the quantitative information comprises data describing structural changes and functional changes associated with regions of interest in the set of scans. The treatment plan generator compares the quantitative information with a set of treatment signatures to determine the patient rate of response. A treatment signature comprises structural changes and functional changes that are expected to occur during the course of a given treatment.

The neuroimage analyzer may also receive a set of brain scans for a plurality of patients in various demographic groups having an identified neuropsychiatric condition and undergoing a given therapy. The set of brain scans comprises scans taken over a given period of time. The neuroimage analyzer analyzes the set of brain scans for the plurality of patients to generate the threshold expected rate of response to the given therapy.

In yet another embodiment, the treatment plan generator analyzes the portions of the medical literature and the set of changes to determine a patient rate of response associated with each therapy in the current treatment plan. The given therapy is a therapy to treat a given condition. In response to the patient rate of response associated with a given therapy falling below a threshold rate of response for the given therapy, the treatment plan generator identifies a set of alternative therapies for the given condition; and the treatment plan generator generates the modified treatment plan using the set of alternative therapies for the given condition. In another embodiment, the treatment plan generator presents the modified treatment plan with a set of links. The set of links to relevant portions of the medical literature associated with each therapy in the modified treatment plan.

BRIEF DESCRIPTION OF THE SEVERAL VIEWS OF THE DRAWINGS

FIGS. 3A and 3B is a block diagram of a neuroimage mapping manager and treatment plan generator in accordance with an illustrative embodiment;

FIG. 11 is a flowchart illustrating a process for correlating changes in brain scans with medical literature and clinical data in accordance with an illustrative embodiment.

DETAILED DESCRIPTION OF THE INVENTION

Figure 1:
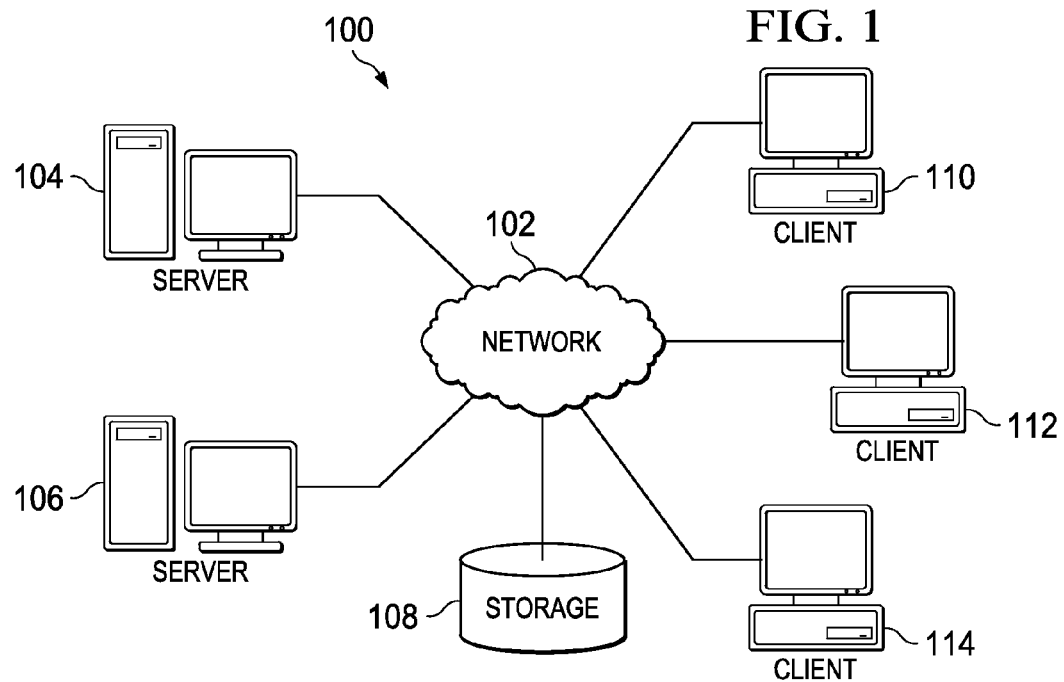
FIG. 1 is a pictorial representation of a network of data processing systems in which illustrative embodiments may be implemented.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, or device. More specific examples (a non-exhaustive list) of the computer-readable medium would include the following: a portable computer diskette, a hard disk, a random access memory (RAM), a read-only memory (ROM), an erasable programmable read-only memory (EPROM or Flash memory), a portable compact disc read-only memory (CDROM), an optical storage device, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, or physically transport the program for use by or in connection with the instruction execution system, apparatus, or device.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Figure 2:
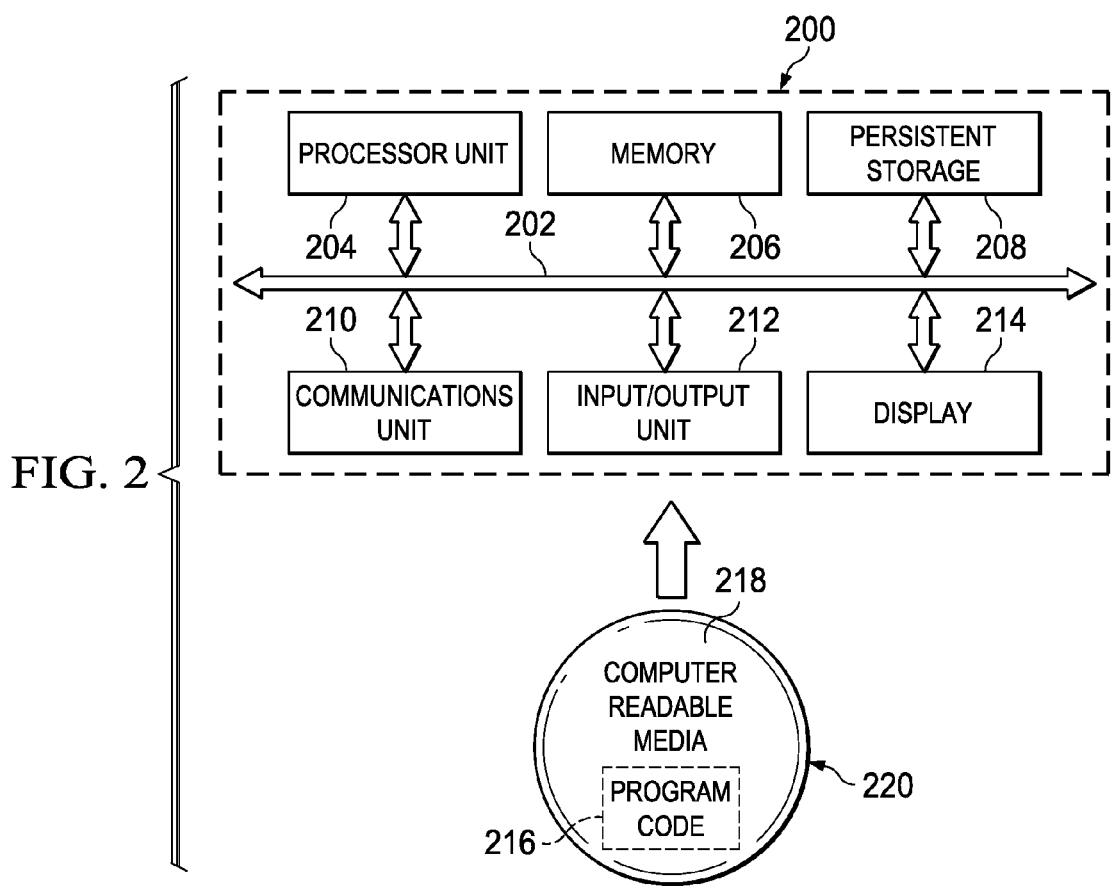
FIG. 2 is a block diagram of a data processing system in which illustrative embodiments may be implemented.

With reference now to the figures and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

With reference now to FIG. 2, a block diagram of a data processing system is shown in which illustrative embodiments may be implemented. Data processing system 200 is an example of a computer, such as server 104 or client 110 in FIG. 1, in which computer usable program code or instructions implementing the processes may be located for the illustrative embodiments. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices. A storage device is any piece of hardware that is capable of storing information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer recordable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communications links or wireless transmissions containing the program code.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown.

As one example, a storage device in data processing system 200 is any hardware apparatus that may store data. Memory 206, persistent storage 208, and computer readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

The illustrative embodiments recognize that it is sometimes difficult for medical practitioners to develop an effective treatment plan in complex cases involving multiple neuropsychiatric conditions, drug interactions, pre-existing conditions that may be impacted by treatments, allergies, new therapies, side-effects, interactions of different therapies when applied together to treat a patient, new medical study results, and other factors that may influence selection of treatments to be used on a particular patient. Moreover, gathering the most up-to-date medical information associated with each therapy that is available so that the medical practitioner can make the best informed treatment decisions may be time consuming and burdensome on the medical practitioners.

In addition, the illustrative embodiments recognize that each individual may react differently to the same therapy. Even when a patient is provided with therapies that are intended to improve the patient's condition, the patient may not respond to the therapies as expected. In other words, a given patient may not respond to a given set of therapies in the same way that another patient responds to the same set of therapies. Moreover, a patient's condition may change during the course of the treatment. For example, the patient may be diagnosed with a new condition that may require a new set of therapies to treat the new condition.

Therefore, in one embodiment, a computer implemented method, apparatus, and computer program product for modifying neuropsychiatric treatment plans based on efficacy of treatment is provided. A current treatment plan for a patient is retrieved. The current treatment plan comprises a first set of therapies to treat a set of neuropsychiatric conditions and portions of the medical literature associated with the set of neuropsychiatric conditions. As used herein, the term "set" refers to one or more, unless indicated otherwise. Thus, in this embodiment, the first set of therapies may include a single therapy, as well as two or more therapies. A therapy is an available therapy that may be used to treat a particular condition. A therapy is not required to cure the condition. A therapy may be a cure or a therapy may only be a treatment intended to improve the quality of life of a patient, reduce appearance of symptoms, reduce the severity of symptoms, reduce the frequency of occurrence of symptoms, improve the functionality of the patient, or otherwise provide a benefit to the patient.

A set of brain scans of the patient is analyzed to determine a set of changes over time associated with the set of neuropsychiatric conditions. The set of scans comprises a first set of scans taken at a first time and a second set of scans taken at a second time. The treatment plan generator analyzes the portions of the medical literature associated with the set of neuropsychiatric conditions and the set of changes associated with the neuropsychiatric conditions to determine a patient rate of response to the treatment plan. In response to the patient rate of response to the treatment plan falling below a threshold expected rate, the treatment plan generator identifies a set of alternative treatments for the patient. The treatment plan generator generates a modified treatment plan. The modified treatment plan comprises the set of alternative treatments.

In one embodiment, the treatment plan generator generates the modified treatment plan by identifying potential therapies associated with the treatment of each diagnosed condition in a set of diagnoses for the patient. The treatment plan generator selects a set of recommended therapies from the potential therapies based on portions of the medical literature describing each therapy in the potential therapies and a medical history for the patient. The set of recommended therapies may be a single therapy, as well as two or more different therapies. A therapy in the set of recommended therapies may include, without limitation, talk therapy, behavioral therapy, chemical therapy, and/or mechanical therapy. The set of recommended therapies may include a single therapy for each neuropsychiatric condition or include two or more recommended therapies for a single neuropsychiatric condition identified in the set of diagnoses. The set of recommended therapies may also include a recommendation that no therapies be applied to treat a particular identified condition in the set of diagnoses. A recommendation of no therapy may be made if no therapies are available to treat the condition or if the therapy may be more harmful than beneficial to the patient due to harmful side effects, negative impact on pre-existing conditions, harmful drug interactions, allergies, or previous negative reaction to a given therapy.

In other words, if a given condition has only been successfully treated with a particular drug therapy and the drug therapy has known side-effects that are likely to exacerbate a pre-existing condition, the drug therapy may not be a viable option. For example, certain antidepressants have a negative drug interaction with Lithium. Therefore, if a patient is taking Lithium for a pre-existing condition, a therapy for a newly diagnosed condition that calls for utilization of antidepressants known to have the negative drug interaction with Lithium are not included in the treatment plan. If no other therapy is available, the best treatment for the newly diagnosed condition may be no treatment at all. However, if other treatments, such as talk therapy may be beneficial, the treatment plan generator may include talk therapy in the set of recommended therapies for the newly diagnosed condition. The treatment plan generator generates the modified treatment plan based on the set of recommended therapies to treat each diagnosed condition in the set of diagnoses. The modified treatment plan may include all the therapies in the set of recommended therapies. In another embodiment, the modified treatment plan may only include one or more of the therapies in the set of recommended therapies.

The treatment plan generator presents the modified treatment plan to a user with a link to relevant portions of the medical literature associated with each therapy in the treatment plan. A link may be a link to a source on a network, such as a hyperlink, or a link to a source on a local data storage device. The treatment plan optionally comprises an identification of negative drug interactions, side effects, allergic reactions, and negative effects on pre-existing conditions of the patient that are associated with each therapy in the treatment plan. In another embodiment, the treatment plan comprises a plurality of therapies recommended for treatment of each neuropsychiatric condition identified in the set of diagnoses. In other words, if a patient is diagnosed with depression and schizophrenia, the modified treatment plan may include one or more therapies for depression and one or more therapies for schizophrenia.

In one embodiment, the selection of a set of recommended therapies from the potential therapies based on portions of the medical literature describing each therapy in the potential therapies and a medical history for the patient further comprises identifying a therapy in the potential therapies that cannot be applied in conjunction with at least one other therapy in the potential therapies to form an inapplicable therapy and removing the inapplicable therapy from the set of potential therapies. The other therapy may be a talk therapy, a pharmacotherapy/drug therapy, a mechanical therapy, or any other type of therapy. As used herein, the term "at least one" refers to a one, as well as two or more. Therefore, "at least one other therapy" refers to one or more other therapies. The one or more other therapies may be the same therapy or a combination of different therapies. For example, and without limitation, the at least one therapy may be two other drug therapies or a combination of a pharmacotherapy and a mechanical therapy.

The selection of recommended therapies may also include the treatment plan generator receiving the medical history. In this embodiment, the medical history comprises an identification of allergens of the patient. An allergen is a substance that has triggered an allergic reaction in the patient. The treatment plan generator identifies any therapy associated with an allergen and removes the identified therapy from the set of recommended therapies.

In another embodiment, the treatment plan generator receives information describing drug interactions and a list of drugs currently being taken by the patient. The treatment plan generator identifies a therapy in the potential therapies that includes utilization of a drug that produces a negative drug interaction with a drug on the list of drugs currently being taken by the patient and automatically removes the therapy from the set of recommended therapies. In yet another embodiment, the treatment plan generator identifies any therapy that may be a cause of a negative impact on a pre-existing condition of the patient and automatically removes the therapy from the set of recommended therapies.

In yet another embodiment, a neuroimage mapping manager receives a set of scans for the patient and automatically analyzes the set of scans to identify regions of interest. The neuroimage mapping manager identifies brain architecture and brain metabolism based on characteristics in the regions of interest and generates the set of diagnoses based on the characteristics in the regions of interest, the brain architecture, and the brain metabolism.

Figure 3B:
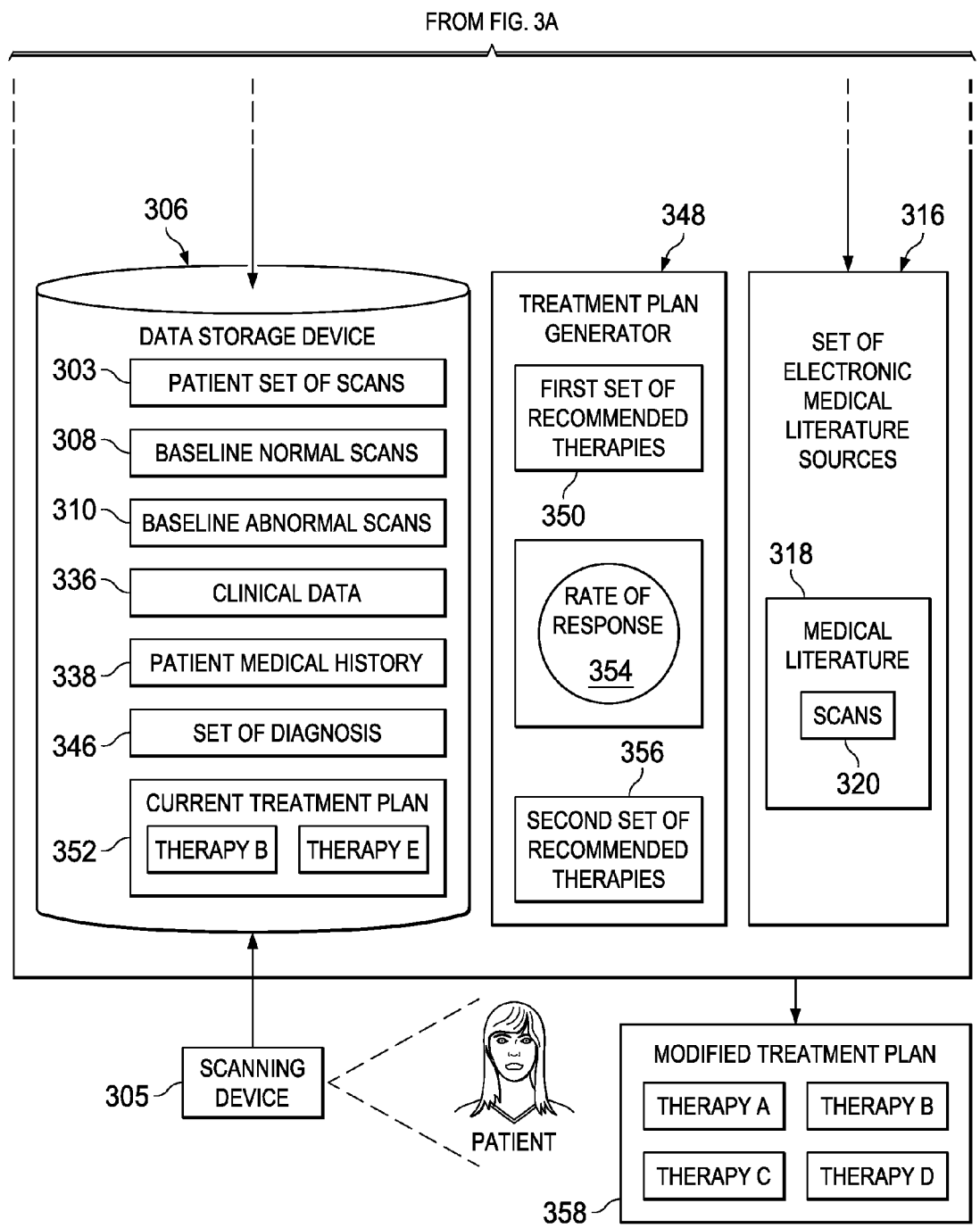

FIGS. 3A and 3B is a block diagram of a neuroimage mapping manager in accordance with an illustrative embodiment. Neuroimage mapping manager 300 is software for analyzing patient brain scans to identify regions of interest in the brain scans and generate links to portions of interest in the medical literature. Computer 301 may be implemented in any type of computing device, such as, without limitation, a server, a client, a laptop computer, a personal digital assistant (PDA), a smart phone, or any other known or available computing device shown in FIG. 1 and FIG. 2.

Neuroimage analyzer 302 receives first set of scans 303. First set of scans 303 is a set of one or more scans of a patient's brain generated at a first time. The first time may be a time prior to beginning implementation of one or more therapies or a given time after beginning one or more therapies. Second set of scans 304 is a set of scans of the patient generated at a second time. The second time is a given period of time after the first time. The second time may be, for example and without limitation, a day, a week, a month, six months, a year, two years, or any other time period after the first time. The second time is a given amount of time after beginning implementation of one or more therapies in a treatment plan to treat a patient.

First set of scans 303 and second set of scans 304 may include functional magnetic resonance imaging (FMRI) scans, structural magnetic resonance imaging (sMRI) scans, positron emission tomography (PET) scans, and/or any other type of brain scans. In other words, first set of scans 303 may include only positron emission tomography scans, only magnetic resonance imaging scans, or a combination of positron emission tomography scans and magnetic resonance imaging scans. The scans in first set of scans 303 may be generated by one or more scanning devices, such as scanning device 305.

Scanning device 305 may be implemented as one or more of a functional magnetic resonance imaging device, a structural magnetic resonance imaging device, a positron emission tomography device, or any other type of device for generating scans of a human patient's brain. As used herein, the term "patient" is not limited to a patient admitted in a hospital. The term "patient" may refer to any person obtaining medical care, consulting a medical practitioner, participating in a medical study, obtaining medical advice, or otherwise participating in medical tests and/or medical procedures.

Scanning device 305 in this example is a single scanning device. However, scanning device 305 may also include two or more scanning devices. Scanning device 305 optionally saves the scans of the patient's brain in data storage device 306. Data storage device 306 may be implemented as a hard drive, a flash memory, a main memory, read only memory (ROM), a random access memory (RAM), or any other type of data storage device. Data storage may be implemented in a single data storage device or a plurality of data storage devices. Thus, neuroimage analyzer 302 may receive the scans in first set of scans 304 from scanning device 305 as each scan is generated, or neuroimage analyzer 302 may retrieve the scans from a pre-generated set of scans stored in data storage device 306.

Comparator 307 is a software component that compares first set of scans 304 to baseline normal scans 308 and/or baseline abnormal scans 310 to identify regions of interest 312 first set of scans 303 and regions of interest 313 in second set of scans. A region of interest is an area in a scan that shows an indication of a potential abnormality, a potential illness, a potential disease, a potential condition, or any other deviation from what would be expected in a scan of the region for a healthy individual having similar characteristics as the patient. The similar characteristics may include, without limitation, an age range of the patient, gender, pre-existing conditions, or other factors influencing the development, function, structure, and appearance of an area of the brain as shown in a scan.

Baseline normal scans 308 may include, without limitation, a set of one or more brain scans for average, healthy subjects having one or more characteristics in common with the patient. The characteristics in common may be age, gender, pre-existing conditions, profession, place of residence, nationality, or any other characteristic. For example, if the patient is a sixteen year old female, baseline normal scans 308 may include scans of normal, healthy female subjects between the ages of fourteen and eighteen. Comparator 307 compares one or more areas in each scan in first set of scans 303 with corresponding areas in one or more scans in baseline normal scans 308 to identify areas of the patient's scans that are consistent with the scans of normal, healthy subjects and to identify areas of the scans that are inconsistent with the scans of normal, healthy subjects. An area in a scan that is inconsistent with the corresponding areas in baseline normal scans 308 are identified as a region of interest in regions of interest 312. A region identified in regions of interest 312 and 313 may indicate a potential abnormality, illness, or condition. However, each region in regions of interest 312 and/or 313 are not required to definitively indicate an abnormality, illness, condition, or other deviation from the norm.

Baseline abnormal scans 310 is a set of one or more scans of subjects having one or more characteristics in common with the patient and diagnosed with an identified condition. The identified condition may be a disease, an illness, a deformity, an abnormality, or any other identified deviation from the norm. For example, if the patient is a male, age thirty five, and diagnosed with diabetes, the baseline abnormal scans may include scans of male patients between the ages of thirty and forty and having a variety of known neuropsychiatric disorders. Comparator 307 compares regions in each scan in first set of scans 303 with one or more scans in baseline abnormal scans 310 to identify regions of interest in the patient's scans that show indications of disorders, illness, disease, or abnormalities. A region in a scan may show indications of a potential illness, condition, abnormality, or neuropsychiatric disorder if the region in the patient's scan is consistent with a corresponding region in a brain scan of a subject having a known illness, condition, abnormality, or neuropsychiatric disorder. Thus, neuroimage analyzer 302 analyzes first set of scans 303 to identify regions of interest in the scans based on baseline normal scans and/or baseline disorder scans for identified illnesses, abnormalities, diseases, disorders, or other known conditions.

Medical data and text analytics 314 is a software component for searching set of electronic medical literature sources 316 for medical literature relevant to regions of interest 312 in first set of scans 304. Set of electronic medical literature sources 316 is a set of one or more sources of medical literature 318. Set of electronic medical literature sources 316 may include both online medical literature sources that are accessed by medical data and text analytics 314 via a network connection, as well as off-line medical literature sources that may be accessed without a network connection. An example of an electronic medical literature source includes, without limitation, PUBMED. Medical literature 318 is any literature, journal article, medical study results, medical text, pharmaceutical studies, or any other medical information in an electronic format. Medical literature 318 may include scans 320, such as magnetic resonance imaging scans, positron emission tomography scans, or any other type of brain scans.

Medical data and text analytics 314 comprises search engine 322. Search engine 322 is any type of known or available information retrieval software for locating medical literature that is relevant to regions of interest 312 in set of electronic medical literature sources 316. Search engine 322 may be software for searching data storage devices on a computer system or a web search tool for searching for medical information on the World Wide Web. Search engine 322 may also make queries into databases, information systems, and other medical literature information sources to locate information relevant to regions of interest 312.

Data mining 324 is a software tool for searching through information available from one or more sources and retrieving medical information relevant to regions of interest 312. Data mining 324, search engine 322, or any other software for locating relevant information may be used to search set of electronic medical literature sources 316 for relevant medical literature. Searching through the information from one or more sources may include, without limitation, using at least one of data mining, search engines, pattern recognition, queries to identify the relevant medical literature in the medical literature available from the set of electronic medical literature sources, data mining cohort, pattern recognition cohort, search engine cohort, or any other cohort appliance of interest. The term "at least one" refers to one or more. For example, searching may include using data mining, search engines, and queries. In another example, searching may include pattern recognition and queries, or any other combination.

A cohort is a group of one or more objects having a common characteristic. For example, a data mining cohort may be, without limitation, a group of one or more objects associated with performing data mining techniques to identify desired data from a data source. A pattern recognition cohort may be, without limitation, a group of pattern recognition software applications that identify patterns in data, such as medical data.

Parser 326 is software for parsing medical literature 318 text into a form suitable for further analysis and processing. Parser 326 may be implemented as any type of known or available parser. Correlation engine 328 correlates portions of medical literature 318 with regions of interest 312 to form portions of medical literature 318 that are relevant or associated with regions of interest 312. A portion of medical literature is a section of medical literature text and/or one or more scans that describes a region of interest, describes a condition, illness, deformity, abnormality, disease, or other cause for an appearance of a region of interest, an area in a scan that is the same or similar to an area of interest, an area in a scan in scans 320 or a portion of text in a medical literature document that is otherwise associated with a characteristic, feature, structure, indicator of brain chemistry, indicator of brain function, or other feature shown in an area of interest in a patient's brain scan.

For example, if a region of interest in patient's brain scan indicates an enlargement of a brain ventricle, a scan in scans 320 in medical literature 318 showing a similar enlargement of the brain ventricle is a portion of medical literature that is relevant or associated with regions of interest 312. Likewise, if a section of a medical journal article in an electronic format in medical literature 318 describes various causes of enlargement of a brain ventricle, that section of the medical literature is also relevant or associated with regions of interest 312. Thus, in this example, portions of medical literature 318 include both the scan showing the enlargement of the ventricle in a different patient and the portion of the medical journal article discussing possible causes of an enlargement of the ventricles in patients.

In this manner, medical data and text analytics 314 is capable of automatically searching for electronic medical literature, identifying portions of the medical literature that are relevant to a particular patient's diagnosis and/or treatment, and correlate each item, such as a scan or a section in a journal article, to each region of interest in the patient's brain scans. When a user wishes to view all the relevant medical literature associated with a particular region of interest, the user can simply request all the portions of medical literature correlated to the particular region of interest. In response, neuroimage mapping manager 300 only provides the portions of medical literature 318 from a plurality of medical literature sources that may be useful to the user, rather than providing the full text of all medical journal articles that have certain key words or search phrases, as is currently done.

Neuroimage mapping manager 300 may also generate a set of links to portions of medical literature 318 describing or associated with regions of interest 312 and/or regions of interest 313. Regions of interest 312 and/or 313 may also optionally include an identification of a source and/or citation for the source of each portion of medical literature linked to the regions of interest. The set of links to portions of medical literature 318 may be embedded in first set of scans 303 and/or second set of scans 304, or embedded within regions of interest 312 in first set of scans 303 and/or regions of interest 313 in second set of scans 304. The set of links to portions of medical literature 318 may also optionally be presented as a separate result apart from first set of scans 304 and/or apart from regions of interest 312. In another embodiment, the set of links to portions of medical literature 318 are embedded in an electronic medical file for the patient or a file for brain scan results for one or more patients. A user selects a link in the set of links to view a portion of medical literature associated with a region of interest. In such a case, the portions of medical literature 318 in the patient's medical file may include a set of links to first set of scans 303 and second set of scans 304 and/or a set of links to regions of interest 312 and 313. In such a case, each portion of the medical literature, such as a scan or a section of a medical journal article, may include a link to the region of interest that is associated with or relevant to that portion of the medical literature. Likewise, all the portions of the medical literature that are relevant to a particular region of interest may include a single link to that particular region of interest rather than each portion of the medical literature including a separate link to the particular region of interest or regions of interest associated with the portions of the medical literature.

The portion of medical literature may be a scan only, text only, or a combination of text and one or more scans. The portion of medical literature may be an entire or complete item, such as a complete medical journal article or a complete section of a medical textbook, if the entire journal article or complete section of the medical text is relevant to the features shown in a particular region of interest. The portion of medical literature may also be a portion of a journal article, a portion of a section of a medical textbook, or other part of an item of medical literature. In such a case, a user may optionally select to view the entire journal article or the entire medical text rather than viewing only the relevant portion of the journal article or medical text.

In this embodiment, baseline normal scans 308 and baseline abnormal scans 310 are pre-generated and available for retrieval from data storage device 306. However, in another embodiment, medical data and text analytics 314 searches set of electronic medical literature sources 316 for scans of normal, healthy subjects to create baseline normal scans 308. Medical data and text analytics 316 also searches set of electronic medical literature sources 316 for scans of subjects having known abnormalities, deformities, illnesses, ailments, diseases, or other neuropsychiatric disorders to create baseline abnormal scans 310.

Thus, neuroimage mapping manager 300 provides data and text analytics to automatically determine regions of a patient's brain affected by neuropsychiatric conditions and/or other illness or abnormality as depicted in functional neuroimage data. Neuroimage data is data associated with a brain scan, such as functional magnetic resonance imaging and positron emission tomography scans. Neuroimage mapping manager 300 applies technologies to data, such as heuristics, which automatically correlate the features identified in regions of interest 312 with relevant portions of medical literature 318 that describes regions of interest 312.

Comparator 307 also compares regions of interest 312 in first set of scans 304 with regions of interest 314 in second set of scans 305 to identify one or more changes in the regions of interest 332 over time. Changes in regions of interest 332 is an identification of changes or differences in the regions of interest in first set of scans 303 and second set of scans 304. For example, if a comparison of first set of scans 303 with second set of scans 304 shows that brain metabolism in a first region of interest has increased and a disruption of activity has occurred in a second region, these changes are identified in change in regions of interest 332. Change in regions of interest 332 may also include a set of links to portions of medical literature 318 associated with or describing the changes.

Input/output 334 may be implemented as any type of input and/or output device for presenting output to a user and receiving input from a user. For example, input/output 334 may present regions of interest 312 to a user and/or receive a selection of one or more regions of interest from a user. Input/output 334 may also be used to present set of diagnoses, treatment plans, or other information to a user. Neuroimage analyzer 302 may optionally present the automatically selected regions of interest to the user using input/output 334. The automatically selected regions of interest may be presented using a display device to present the regions of interest in a visual format, using an audio device to present the regions of interest to the user in an audio format, using a tactile interface that may be read by the visually impaired, using a combination of audio and visual devices, using a combination of audio and tactile devices, or any other presentation device.

The user may utilize input/output 334 to choose to select one or more additional regions of interest in first set of scans 303 and/or second set of scans 304. In such a case, neuroimage analyzer 302 adds the manually selected set of one or more regions of interest to regions of interest 312. In one embodiment, the regions of interest that are not automatically selected by neuroimage analyzer 302 and/or regions of interest that are not manually selected by the user are automatically removed by neuroimage analyzer 302. In another embodiment, the user may choose to manually de-select or remove one or more regions of interest that was automatically selected by neuroimage analyzer 302. In such a case, neuroimage analyzer 302 automatically removes the one or more regions of interest selected for removal by the user from regions of interest 312.

In another embodiment, neuroimage mapping manager 300 makes a determination as to whether indicators correlate with the patient's clinical data. Clinical data 336 is data describing the results of clinical laboratory tests. Clinical data 336 may include, without limitation, urinalysis tests, blood tests, thyroid tests, biopsy results, cultures, electrolyte tests, genetic tests, bone marrow tests, tests for the presence of viral agents/illness, tests for the presence of bacterial agents/illnesses, hormone tests, or any other type of laboratory tests. Clinical data 336 describes the presence of substances in the blood, urine, tissue, hormone levels, body chemistry, and body fluids. Clinical data 336 may be relevant to diagnosis or therapy for a particular condition.

Moreover, clinical data 336 may reveal causes of one or more features in the brain scans. For example, clinical tests may indicate mercury poisoning or other substances in the blood that may be responsible for the abnormal appearance of a region in a brain scan. Clinical data 336 for a particular patient may be available on data storage device 306, obtained from a remote data storage device via a network connection, and/or may be manually input to neuroimage mapping manager through input/output device 334. If the features in a region of interest correlate with clinical data 336, neuroimage mapping manager 300 identifies the correlations in result 332. The correlations may be provided as links to information embedded within regions of interest 312 and/or 313 or provided separately from the regions of interest.

Patient medical history 338 is a record of the patient's past and current medical treatments, prescribed drugs, medical procedures, diagnoses, treating physicians, known allergies, and/or any other medical information associated with the patient. Neuroimage mapping manager 300 may correlate information in patient medical history that may be responsible for an appearance or presence of a feature in a region of interest with that particular region in regions of interest 312.

For example, if patient medical history 338 indicates that the patient suffered a head trauma in a car accident when the patient was a child that led to structural damage in a particular area of the brain, that information is linked to the region of interest corresponding to the area of the brain where the head trauma occurred. Likewise, if the patient had brain surgery to prevent or lessen the effects of seizures and the epilepsy surgery effects brain function in one or more areas of the brain, the regions of interest that are correlated to the areas of the brain effected by the epilepsy surgery are identified in regions of interest 312 with a link to the portion of the patient's patient medical history 338 discussing the epilepsy surgery and effects of the epilepsy surgery.

In another embodiment, neuroimage mapping manager 300 makes a determination as to whether changes in regions of interest 332 correlate with the patient's clinical data or medical history. For example, clinical tests may indicate mercury poisoning or other substances in the blood that may be responsible for the changes in brain chemistry and/or brain function shown in the brain scans. If the changes in regions of interest 332 correlate with the clinical data or medical history, neuroimage mapping manager 300 identifies the correlations in change in regions of interest 332 or the correlations may be identified in a separate output provided separately from change in regions of interest over time 332.

A diagnostic engine (not shown) may optionally analyze regions of interest 312 and 312, portions of medical literature 318, clinical data 336, patient medical history 338, as well as any other patient data to automatically identify indicators of potential neuropsychiatric conditions. An indicator includes, without limitation, a symptom, a behavior, a test result, a feature of a brain scan, or any other indicator of a given condition. Indicators of neuropsychiatric conditions may include, for example, and without limitation, levels of brain metabolism, structural features of the brain, functional aspects of the brain, behavioral tics, levels of chemicals, such as dopamine and neurotransmitters, and other indicators of neuropsychiatric conditions.

The diagnostic engine may compare the set of indicators of potential neuropsychiatric conditions with diagnostic signatures. A diagnostic signature is a signature that corresponds to at least one indicator in the set of indicators. The diagnostic signatures are generated automatically by the diagnostic engine by analyzing medical literature 318 and scans 320 of patients with known neuropsychiatric disorders to identify indicators or signatures of each known neuropsychiatric disorder. For example, and without limitation, if a majority of patients diagnosed with schizophrenia have enlarged brain ventricles, enlarged brain ventricles are identified as a signature of schizophrenia.

The diagnostic engine may also attach a weighting to each signature. For example, if a majority of patients diagnosed with schizophrenia have the enlarged brain ventricles but only thirty percent of patients diagnosed with schizophrenia have a decreased level of metabolism in a particular region of the brain, the diagnostic engine may assign a higher weighting to a signature of enlarged brain ventricles than a signature for decreased metabolism in the particular region of the brain. The diagnostic engine optionally uses the weighting to identify each diagnosis in set of diagnoses 346 for the patient.

In another embodiment, a user may manually input one or more diagnosis in set of diagnoses 346. In other words, rather than the diagnostic engine generating all the diagnosis in set of diagnoses 346, a user may manually provide one or more diagnosis by via input/output 334. A user may also optionally enter one or more signatures for utilization by the diagnostic engine. In other words, rather than the diagnostic engine automatically generating the signatures, a user may manually provide one or more signatures for utilization by the diagnostic engine via input/output 334.

Set of potential diagnoses 346 may include a single diagnosis of one condition, as well as diagnoses for two or more neuropsychiatric conditions. Set of diagnoses 346 may optionally include additional information to permit a user to easily review information associated with the diagnoses. For example, and without limitation, set of diagnoses 346 may include an identification of the indicators of neuropsychiatric conditions, an identification of the matching diagnostic signatures, the weighting assigned to each matching diagnostic signature, regions of interest 312 and/or 313, portions of medical literature 318, relevant portions of clinical data 336, relevant portions of patient medical history 338, and any other information relevant to each diagnosis generated by the diagnostic engine.

In another embodiment, set of potential diagnoses 346 includes a link to the additional information. For example, and without limitation, set of diagnoses 346 may include a link to portions of medical literature 318, a link to regions of interest 312, a link to relevant portions of clinical data 336, a link to relevant portions of patient medical history 338, a link to matching diagnostic signatures and the weighting for each matching diagnostic signature, as well as links to any other relevant data used to generate each diagnosis.

Treatment plan generator 348 is software for automatically generating a treatment plan for the patient based on set of diagnoses 346. Treatment plan generator 348 analyzes relevant portions of medical literature 318 for potential therapies to treat each condition identified in set of diagnoses 346. Treatment plan generator 348 identifies the potential therapies and selects one or more therapies from the potential therapies that are recommended based on regions of interest 312, patient medical history 338, clinical data 336, and any other patient data to form first set of recommended therapies 350. Each therapy in first set of recommended therapies 350 may be associated with drug interactions, side effects, risks based on pre-existing conditions, ingredients that may be allergens, and other contraindications. Treatment plan generator 348 generates current treatment plan 352 using set of recommended therapies 350. Treatment plan 352 may include a single therapy or a plurality of therapies. In this example, treatment plan 352 includes therapy B and therapy E. The therapies may be as talk therapy, behavioral therapy, chemical therapy, and/or mechanical therapy.

In one embodiment, treatment plan generator 348 eliminates any therapies from the set of recommended therapies 350 based on the drug interactions, side effects, risk, allergies, and other contraindications. For example, if a therapy includes use of a drug that includes iodine and patient medical history 338 indicates that the patient is allergic to iodine, treatment plan generator 348 eliminates the therapy from set of recommended therapies. Treatment plan generator 348 generates treatment plan 352 without the therapies that are eliminated from set of recommended therapies 350. In another embodiment, rather than remove the contraindicated therapies from set of recommended therapies 350, treatment plan generator 348 includes information describing the drug interaction, side effects, risk, potential allergic reaction, or other contraindications in treatment plan 352 for review by a user prior to implementation of treatment plan 352.

In another embodiment, treatment plan 352 may also include relevant portions of the medical literature, such as, without limitation, information describing drug interaction warning, side-effects associated with each therapy, dosage recommendations, contraindications, allergy warnings, and an expected response to each therapy by the patient. Treatment plan 352 may also include recommendations as to when each therapy should be administered, a frequency with which each therapy should be administered, drug dosages, and other recommendations for applying the therapies to the patient.

When change in regions of interest 332 becomes available after application of the therapies in current treatment plan 352 has begun or after a given period of time has lapsed since first set of scans 303 was generated, treatment plan generator 348 then analyzes change in regions of interest 332 and portions of medical literature 318 to generate a patient rate of response. The rate of response may be a percentage improvement or decline, a number of episodes, a frequency of symptoms, a rating for patient functionality, a rating for a patient's ability to interact with others, clinical test results, cognitive test results, or any other standard, rating, grade, gauge, or other indicator of a patient's status changes over time. The rating may indicate an improvement in the patient's condition, a decline in the patient's condition, or a lack of any change in the patient's condition.

Treatment plan generator 348 analyzes portions of the relevant medical literature 318, change in regions of interest 332, and current treatment plan 352 to determine rate of response 354. Rate of response 354 may include an overall rate of response for the entire treatment plan as a whole and/or a rate of response by the patient to each therapy in current treatment plan 352. Treatment plan generator 348 may also analyze current treatment plan 352 for indicators as to the expected overall response by the patient, the expected rate of response over time, risks and side effects identified with each therapy, and other medical information associated with each therapy.

Treatment plan generator 348 then makes a determination as to whether rate of response 354 is below a threshold. For example, if a drug therapy is expected to reduce the number of seizures and the severity of seizures in the patient, and rate of response 354 indicates that the number of seizures and the severity of the seizures have not been reduced, then the rate of response by the patient may fall below the threshold.

If rate of response 354 has fallen below the threshold, treatment plan generator 348 identifies second set of recommended therapies 356. Second set of recommended therapies is a set of alternative therapies. Second set of recommended therapies includes one or more therapies that may be applied as a substitute for one or more therapies in current treatment plan 352. For example, if a patient's rate of response indicates that the patient is not responding to a given antidepressant, the set of alternative treatments may include one or more alternative antidepressant drugs, include recommendations for talk therapy, and/or other therapies which may alleviate the patient's depression. Treatment plan generator 348 generates modified treatment plan 358 using second set of recommended therapies 356.

Modified treatment plan 358 may include all the therapies in second set of recommended therapies 356 or only one or more therapies selected from second set of recommended therapies 356. Modified treatment plan 358 may also include none of the therapies from current treatment plan 352, include one of the therapies from current treatment plan 352, or include two or more of the therapies in common with current treatment plan 352. As shown in FIG. 3, current treatment plan 352 includes therapy B and therapy E. In response to determining that the patient is not responding as anticipated, treatment plan generator generates modified treatment plan 358 based on second set of recommended therapies 356. In this example, modified treatment plan 358 does not include therapy E but it does include therapy B from current treatment plan 352. Modified treatment plan 358 also includes three new therapies, therapy A, therapy C, and therapy D that were not included in current treatment plan 352. Modified treatment plan 358 is then used to treat the patient rather than current treatment plan 352 which did not result in the desired rate of response by the patient.

After a given period of time following the beginning of administration of the therapies in modified treatment plan 358, treatment plan generator may again analyze changes in the regions of interest occurring since the therapies in modified treatment plan 358 were begun, as well as analyze updated clinical data, medical history, and medical literature to determine if the patient is responding positively to the therapies. If the patient is not responding positively or not responding as well as desired, treatment plan generator 348 may again identify other alternative treatments and generate another modified treatment plan.

Figure 4:
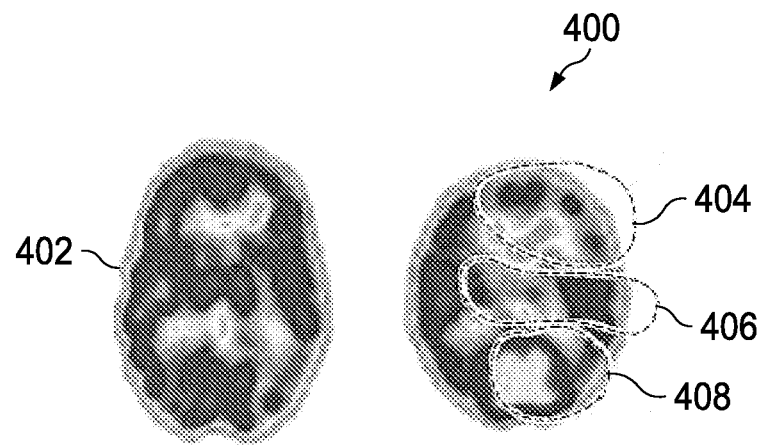
FIG. 4 is a block diagram of a magnetic resonance imaging brain scan having regions of interest in accordance with an illustrative embodiment.

Referring to FIG. 4, a block diagram of a magnetic resonance imaging brain scan having regions of interest is depicted in accordance with an illustrative embodiment. Scan 400 is a positron emission tomography scan of a brain of a patient. Scan 402 is a positron emission tomography scan of a normal, healthy subject. Scan 400 has regions of interest 404-408. Regions of interest 404-408 are areas in scan 400 that show indications of one or more neuropsychiatric conditions, such as, for example and without limitation, schizophrenia. In this example, regions of interest 404-408 show disruptions in brain activity. Region 406 shows abnormal changes in the ventricles of the brain. Region 408 shows decreased function in the frontal section.

Figure 5:
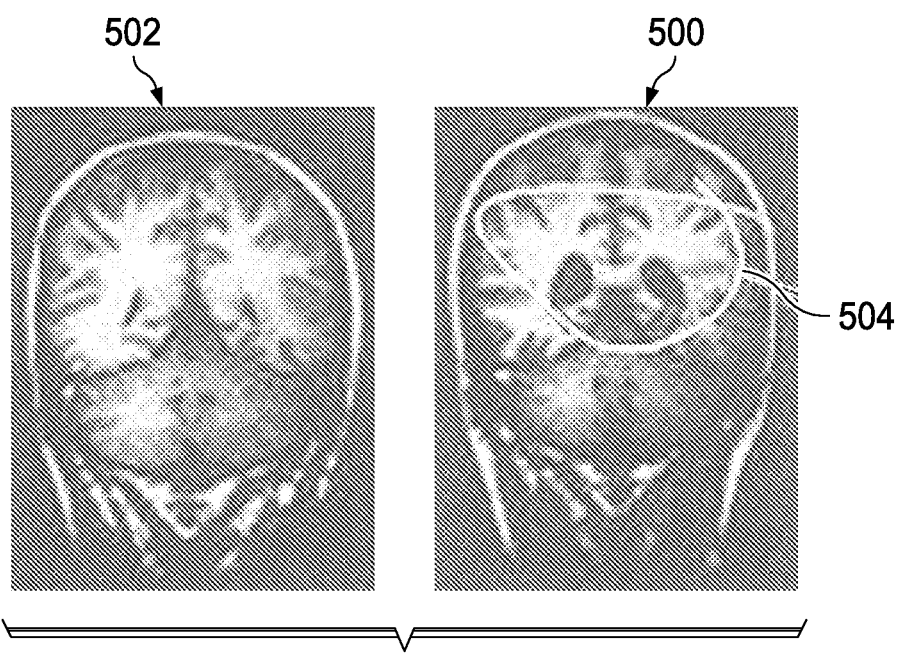
FIG. 5 is a positron emissions tomography brain scan having regions of interest in accordance with an illustrative embodiment.

Turning now to FIG. 5, a positron emissions tomography brain scan having regions of interest is shown in accordance with an illustrative embodiment. Scan 500 is a magnetic resonance imaging scan of a patient's brain. Scan 502 is a magnetic resonance imaging scan of a normal, healthy subject's brain. Scan 500 includes region of interest 504. Region 504 shows an abnormal enlargement of the ventricles of the brain when compared with scan 502 of a normal, healthy subject. The enlargement of the brain ventricles shown in region of interest 504 is an indicator of a neuropsychiatric condition, such as, for example and without limitation, schizophrenia. Therefore, a neuroimage mapping manager identifies region 504 as a region of interest.

Figure 6:
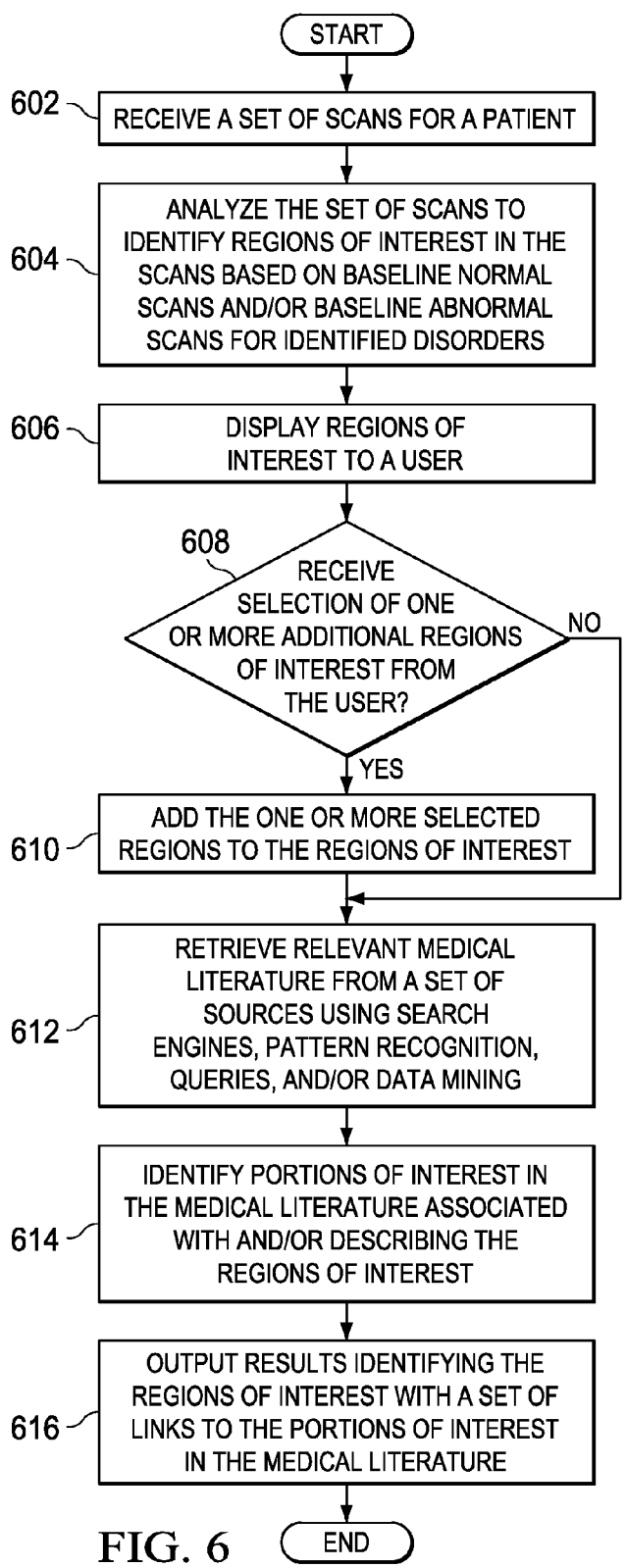
FIG. 6 is a flowchart illustrating a process for analyzing a set of brain scans for a patient to identify regions of interest with links to relevant portions of the medical literature in accordance with an illustrative embodiment.

FIG. 6 is a flowchart illustrating a process for analyzing a set of brain scans for a patient to identify regions of interest with links to relevant portions of the medical literature in accordance with an illustrative embodiment. The process in FIG. 6 may be implemented by software for analyzing patient brain scans to identify regions of interest in the brain scans and generate links to portions of interest in the medical literature, such as neuroimage mapping manager 300 in FIGS. 3A and 3B.

The neuroimage mapping manager receives a set of scans for a patient (step 602). The set of scans may include, without limitation, functional magnetic resonance imaging (FMRI) scans, structural magnetic resonance imaging (sMRI) scans, positron emission tomography (PET) scans, or any other type of brain scans. The neuroimage mapping manager analyzes the set of scans to identify regions of interest in the scans based on baseline normal scans and/or baseline abnormal scans for identified disorders (step 604). The neuroimage mapping manager displays the identified regions of interest to a user (step 606). The neuroimage mapping manager makes a determination as to whether a selection of one or more additional regions of interest is received from the user (step 608).

If a selection of one or more additional regions of interest is received from the user, the neuroimage mapping manager adds the one or more selected regions to the regions of interest (step 610). After adding the selected regions to the regions of interest at step 610 or if no selections of additional regions are received from the user at step 608, the neuroimage mapping manager retrieves relevant medical literature from a set of sources using search engines, pattern recognition, queries, and/or data mining (step 612). The embodiments are not limited to using only search engines, queries, and data mining. Any known or available method for locating desired information in an electronic data source may be utilized.

Next, the neuroimage mapping manager identifies portions of interest in the medical literature associated with and/or describing the regions of interest (step 614). The portions of interest may include pages, paragraphs, or portions of text describing one or more of the regions of interest, the appearance of one or more of the regions of interest, or the characteristics of one or more of the regions of interest. The portions of interest in the relevant medical literature may include images of scans containing one or more of the regions of interest, portions of text in the medical literature describing diseases, deficiencies, illnesses, and/or abnormalities that may cause the appearance of one or more of the regions of interest or one or more characteristics of the regions of interest, or any other portion of medical literature that is relevant to one or more of the regions of interest in the patient's scans. The neuroimage mapping manager outputs results identifying the regions of interest with a set of links to the portions of interest in the medical literature (step 616) with the process terminating thereafter.

In this embodiment, the regions of interest are displayed to the user and the user is given an opportunity to select one or more additional regions of interest to add to the regions of interest identified by the neuroimage mapping manager. In another embodiment, the regions of interest are not presented to the user prior to identifying the portions of interest in the medical literature. In this embodiment, the user is not required to review the regions of interest and provide input as to whether to add one or more additional regions of interest. In this case, the process may occur completely automatically without any user input during the process of analyzing the patient's scans to identify regions of interest and linking portions of the relevant medical literature to the regions of interest.

Figure 7:
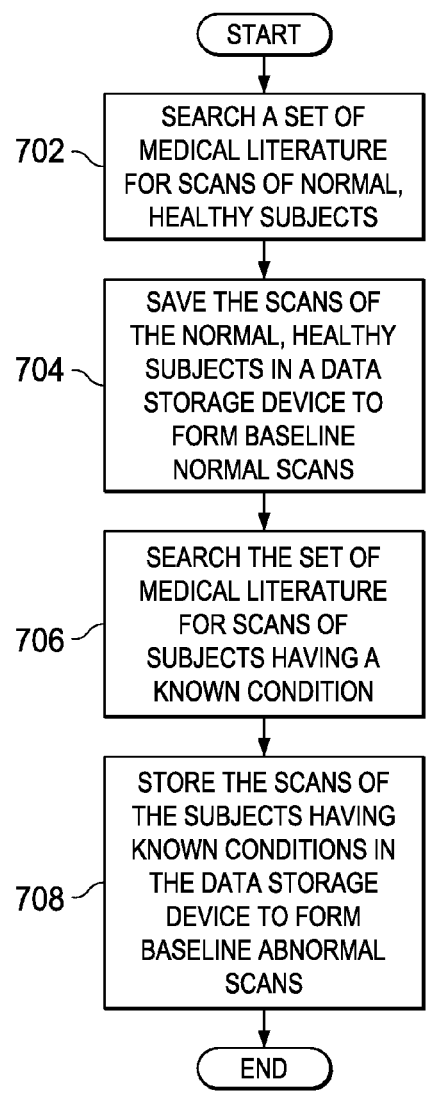
FIG. 7 is a flowchart illustrating a process for generating baseline control scans in accordance with an illustrative embodiment.

Referring now to FIG. 7, a flowchart illustrating a process for generating baseline control scans is shown in accordance with an illustrative embodiment. The process in FIG. 7 may be implemented by software for generating a set of baseline control scans, such as medical data and text analytics 314 in FIGS. 3A and 3B.

The process begins by searching a set of medical literature sources for scans of normal, healthy subjects (step 702). The scans of the normal, healthy subjects are saved in a data storage device to form baseline normal scans (step 704). The process searches the set of medical literature sources for scans of subjects having known conditions (step 706). The conditions may be a disease, an illness, an infection, a deformity, or any other condition. The scans of the subjects having the known conditions are saved in the data storage device to form baseline abnormal scans (step 708) with the process terminating thereafter.

Figure 8:
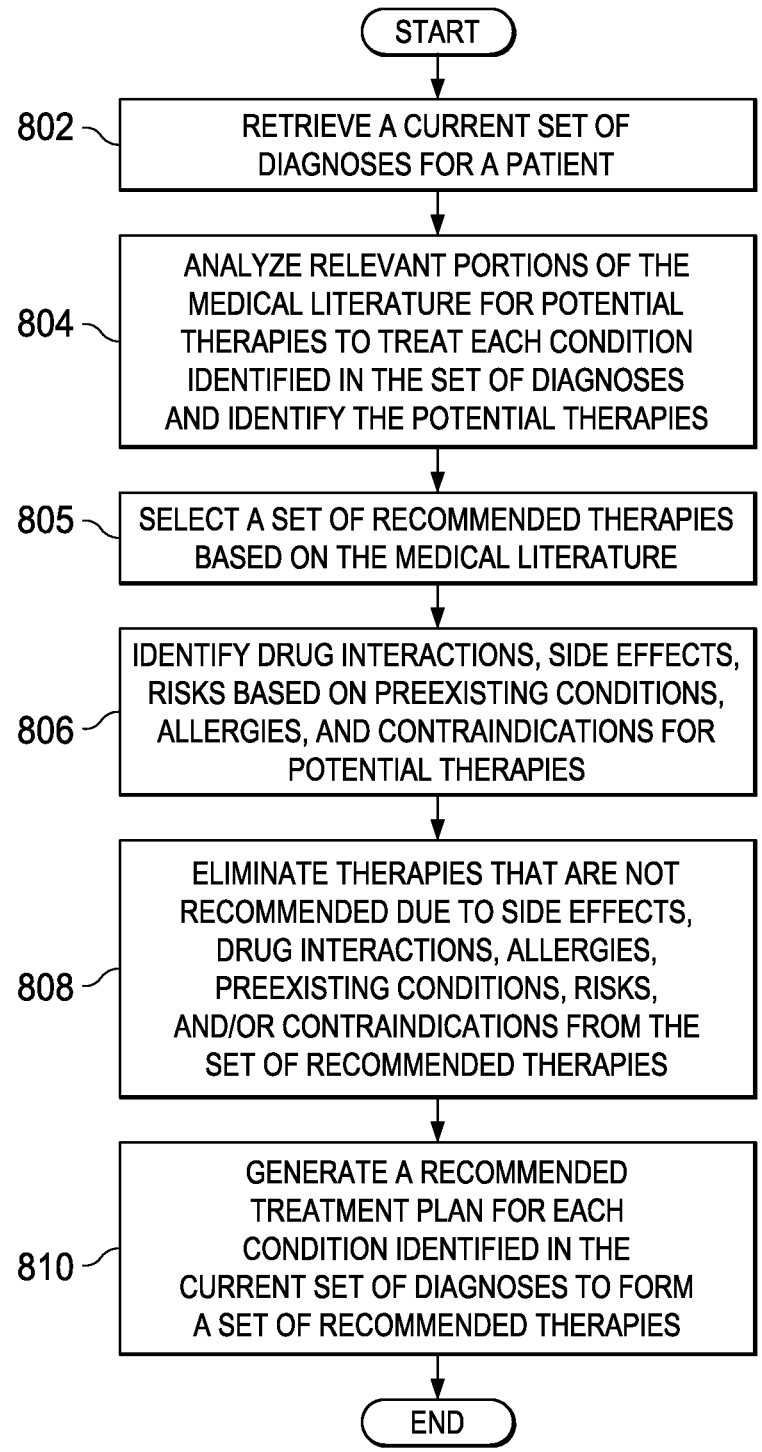
FIG. 8 is a flowchart illustrating a process for automatically generating a treatment plan in accordance with an illustrative embodiment.

FIG. 8 is a flowchart illustrating a process for automatically generating a treatment plan in accordance with an illustrative embodiment. The process in FIG. 8 is implemented by software for automatically generating treatment plans based on neuroimage data, such as, treatment plan generator 348 in FIGS. 3A and 3B.

The process begins by retrieving a current set of diagnoses for a patient (step 802). The treatment plan generator analyzes relevant portions of the medical literature for potential therapies to treat each condition identified in the set of diagnoses and the treatment plan generator identifies the potential therapies (step 804). The treatment plan generator selects a set of recommended therapies based on the medical literature (step 805). The treatment plan generator identifies drug interactions, side effects of therapies in the set of recommended therapies, risks associated with the therapies in the set of recommended therapies based on pre-existing conditions, allergies, and contraindications for the therapies in the set of recommended therapies (step 806). The treatment plan generator eliminates therapies from the set of recommended therapies (step 808). The treatment plan generator generates a recommended treatment plan for each condition identified in the current set of diagnoses (step 810) with the process terminating thereafter.

Figure 9:
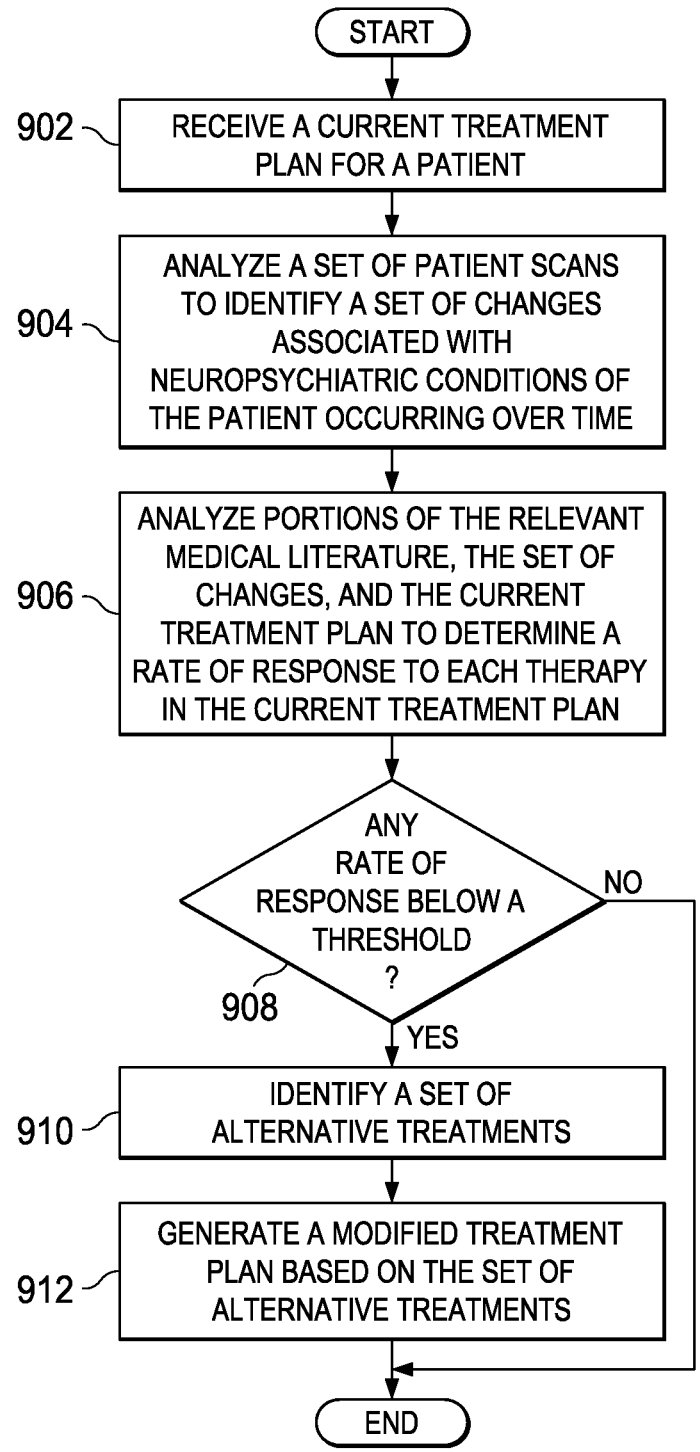
FIG. 9 is a flowchart illustrating a process for automatically modifying a treatment plan based on a patient's response to a set of therapies identified in the treatment plan in accordance with an illustrative embodiment.

FIG. 9 is a flowchart illustrating a process for automatically modifying a treatment plan based on a patient's response to a set of therapies identified in the treatment plan in accordance with an illustrative embodiment. The process in FIG. 9 is implemented by software for automatically generating treatment plans, such as treatment plan generator 348 in FIGS. 3A and 3B. Steps 902-904 may be implemented by software for analyzing brain scans and identifying regions of interest and changes in the regions of interest over time, such as neuroimage analyzer 302 in FIGS. 3A and 3B.

The process begins by receiving a current treatment plan for a patient (step 902). The process analyzes a set of patient scans to identify a set of changes associated with neuropsychiatric conditions of the patient occurring over time (step 904). The set of scans comprises brain scans taken at a first time and brain scans taken at a second time that is a given period of time after the first time. For example, the set of patient scans may include scans generated at an initial examination of the patient and scans generated six months later after the patient has begun one or more therapies recommended in a current treatment plan.

The process analyzes portions of the relevant medical literature, the set of changes in the brain scans, and the current treatment plan to determine a rate of response to each therapy in the current treatment plan (step 906). The current treatment plan is analyzed for indicators as to the expected overall response by the patient, the expected rate of response over time, risks and side effects identified with each therapy, and other medical information associated with each therapy.

The process then makes a determination as to whether the rate of response shown by the patient is below a threshold (step 908). For example, if a drug therapy is expected to reduce the number of seizures and the severity of seizures in the patient, and the rate of response indicates that the number of seizures and the severity of the seizures have not been reduced, then the rate of response by the patient may fall below the threshold.

If the rate of response has fallen below the threshold, the process identifies a set of alternative treatments (step 910). The set of alternative treatments is a set of one or more therapies that may be applied as a substitute for one or more therapies in the current treatment plan. For example, if a patient's rate of response indicates that the patient is not responding to a given antidepressant, the set of alternative treatments may include one or more alternative antidepressant drugs, include recommendations for talk therapy, and/or other therapies which may alleviate the patient's depression.

The process generates a modified treatment plan based on the set of alternative treatments (step 912) with the process terminating thereafter.

Figure 10:
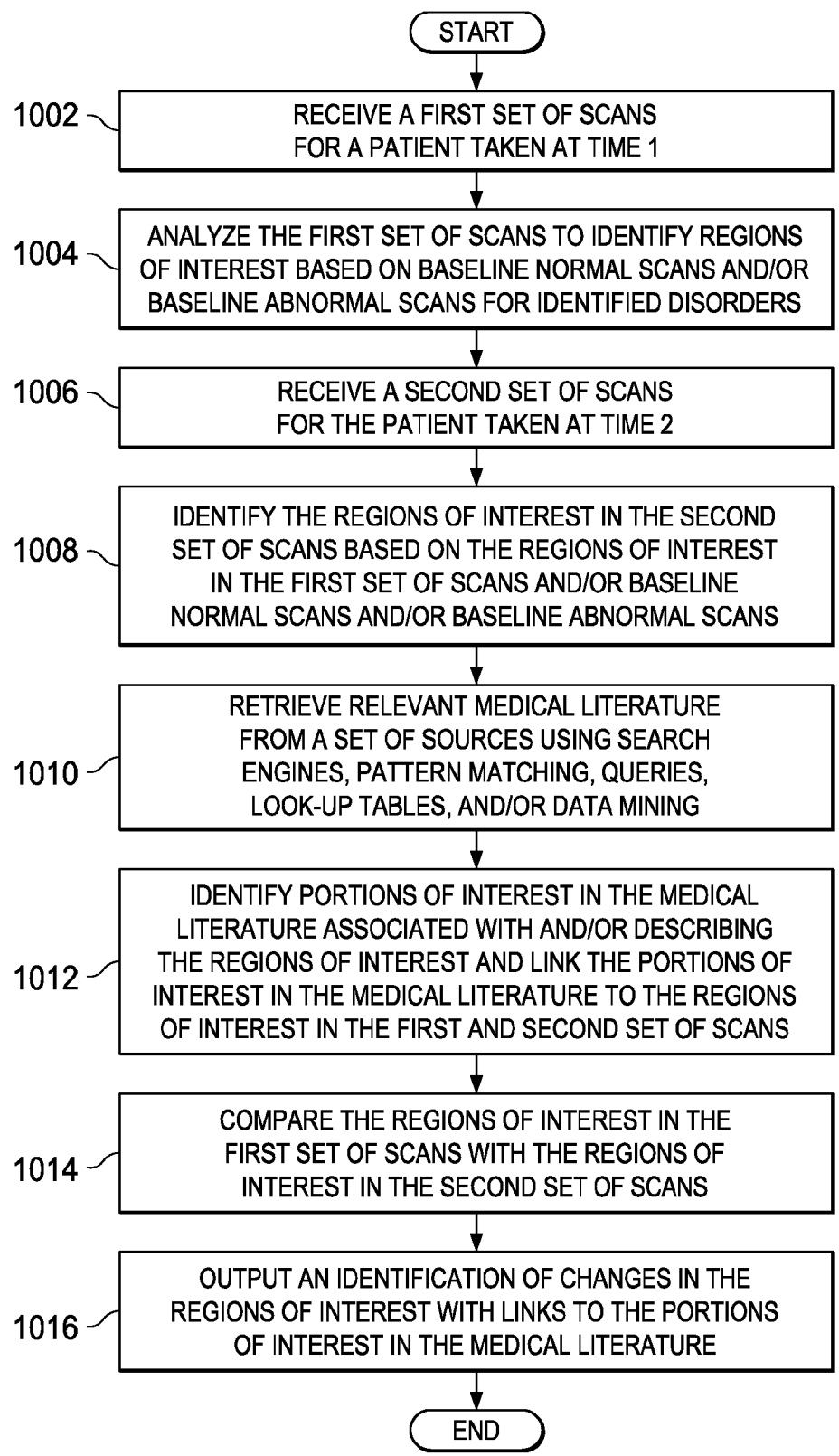
FIG. 10 is a flowchart illustrating a process for identifying changes in regions of interest in brain scans taken at different times and linking portions of interest in relevant medical literature with the regions of interest in the brain scans in accordance with an illustrative embodiment.

Referring now to FIG. 10, a flowchart illustrating a process for identifying changes in regions of interest in brain scans taken at different times and linking portions of interest in relevant medical literature with the regions of interest in the brain scans is depicted in accordance with an illustrative embodiment. The process in FIG. 10 may be implemented by software for identifying changes in regions of interest in patient scans and linking portions of the relevant medical literature, such as neuroimage analyzer 302 in FIGS. 3A and 3B.

The process begins by receiving a first set of scans for a patient taken at time one (step 1002). The neuroimage analyzer analyzes the first set of scans to identify regions of interest based on baseline normal scans and/or baseline abnormal scans for identified disorders (step 1004). The neuroimage analyzer receives a second set of scans for the patient taken at time two (step 1006). The neuroimage analyzer identifies the regions of interest in the second set of scans based on the regions of interest in the first set of scans and/or baseline normal scans and/or baseline abnormal scans (step 1008). The neuroimage analyzer retrieves relevant medical literature from a set of sources using search engines, pattern matching, queries, look-up tables, and/or data mining (step 1010).

The neuroimage analyzer then identifies portions of interest in the medical literature associated with and/or describing the regions of interest and links the portions of interest in the medical literature to the regions of interest in the medical literature to the regions of interest in the first and second set of scans (step 1012). The neuroimage analyzer compares the regions of interest in the first set of scans with the regions of interest in the second set of scans (step 1014). The neuroimage analyzer outputs an identification of changes in the regions of interest with links to the portions of interest in the medical literature (step 1016) with the process terminating thereafter.

In this embodiment, only two sets of scans taken at two times are used. However, in accordance with this embodiment, any number of set of scans taken at different times may be used. For example, and without limitation, a third set of scans taken at a third time and a fourth set of scans generated at a fourth time may also be received and analyzed to identify regions of interest and identify changes in the regions of interest occurring over time.

FIG. 11 is a flowchart illustrating a process for correlating changes in brain scans with medical literature and clinical data in accordance with an illustrative embodiment. The process in FIG. 11 may be implemented by software for correlating medical literature and clinical data with changes in regions of interest in brain scans occurring over time, such as neuroimage mapping manager 300 in FIGS. 3A and 3B.

The neuroimage mapping manager assesses brain chemistry and/or brain metabolism based on functional imaging data (step 1102). The functional imaging data may be obtained from functional magnetic resonance imaging scans, positron emission tomography scans, or any other type of brain scan. The neuroimage mapping manager determines a before and after state of the patient's brain chemistry and/or brain metabolism based on imaging data taken before therapy began and imaging data taken after therapy began (step 1104). The before and after state may be determined by comparing any first set of brain scans taken at a first time period with a second set of brain scans taken at a second time period. For example, and without limitation, the first set of brain scans may be taken prior to beginning therapy or at any point after beginning therapy and the second set of scans may be taken at a time period that is after the time period when the first set of scans were taken. In another example, the second set of scans may be taken a given period of time after the first set of scans, regardless of when therapy began. The second set of scans may be taken, without limitation, a week after the first set of scans, a month after the first set of scans, six months after the first set of scans, a year after the first set of scans, or any other period of time after the first set of scans were generated.

The neuroimage mapping manager correlates the before and after state of the patient's brain chemistry and/or brain metabolism to medical literature and clinical data for the patient using text analytics and heuristics (step 1106). The neuroimage mapping manager makes a determination as to whether changes in the initial scans and scans performed after therapy began are present (step 1108). If there are changes between the initial scans and the second set of scans performed after therapy began, the neuroimage mapping manager makes a determination as to whether the change is a change in metabolism (step 1110). If the change is a change in metabolism, the neuroimage mapping manager determines whether the change is an increase or decrease (step 1112). The neuroimage mapping manager then determines where the change occurred and how much the patient's brain metabolism changed (step 1114).

The neuroimage mapping manager then makes a determination as to whether the changes correlate with the patient's clinical data (step 1116). If the changes correlate with the clinical data, the neuroimage mapping manager identifies the correlations (step 1118) with the process terminating thereafter. The correlations may be identified in the results identifying the regions of interest and the changes in the regions of interest from the initial set of scans to the second set of scans.

Thus, in one embodiment, a computer implemented method, apparatus, and computer program product is provided for developing neuropsychiatric treatment plans. A treatment plan generator receives a set of diagnoses for a patient. The treatment plan generator automatically analyzes medical information in a set of electronic medical literature sources for potential therapies associated with treatment of each identified condition in the set of diagnoses. The treatment plan generator identifies the potential therapies associated with the treatment of each diagnosed condition. The treatment plan generator selects a set of recommended therapies from the potential therapies based on portions of the medical literature describing each therapy in the potential therapies and a patient medical history for the patient. The treatment plan generator generates a treatment plan. The treatment plan comprises the set of recommended therapies to treat each diagnosed condition in the set of diagnoses.

Thus, the treatment plan generator automatically identifies therapies for one or more neuropsychiatric conditions and generates a treatment plan for applying the identified therapies to a patient without requiring input or intervention from a human user. The treatment plan generator lessens the workload on physicians and researchers, permits more accurate data interpretation and analysis of scans, and allows physicians and researchers to more quickly establish treatment plans for patients suffering from neuropsychiatric conditions.

In addition, the treatment plan generator provides a decision support tool for clinicians in both clinical and research settings, to help them identify treatments for neuropsychiatric conditions in complex cases, as well as to determine whether a therapy, such as talk therapy, pharmacotherapy, or mechanical electroconvulsive therapy, will be beneficial in light of drug interactions, side effects, allergies, medical history, pre-existing conditions, neuroimage data, and information available in the medical literature. Moreover, the treatment plan generator maps relevant portions of the medical literature onto a patient's treatment plan for reference prior to, during, and after application of each therapy in the treatment plan.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, or physically transport the program for use by or in connection with the instruction execution system, apparatus, or device.

The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method of modifying treatment plans based on efficacy of treatment, the computer implemented method comprising:

a physical processor retrieving a current treatment plan for a patient, wherein the current treatment plan comprises a first set of therapies to treat a set of neuropsychiatric conditions and portions of medical literature associated with the first set of therapies;

the physical processor analyzing a set of scans of the patient to determine a set of changes over time associated with the set of neuropsychiatric conditions, wherein the set of scans comprises a first set of scans taken at a first time and a second set of scans taken at a second time;

the physical processor analyzing portions of medical literature associated with the set of neuropsychiatric conditions and the set of changes associated with the neuropsychiatric conditions to determine a patient rate of response to the current treatment plan;

the physical processor, responsive to the patient rate of response to the current treatment plan falling below a threshold expected rate, identifying a set of alternative treatments for the patient; and the physical processor generating a modified treatment plan using the set of alternative treatments.

2. The computer implemented method of claim 1 further comprising:

the physical processor presenting a result of analyzing the portions of medical literature associated with the set of neuropsychiatric conditions, the set of changes associated with the neuropsychiatric conditions, and the treatments in the current treatment plan to a user, wherein the result comprises the current treatment plan and a patient rate of response associated with each neuropsychiatric condition in the set of neuropsychiatric conditions; and the physical processor, responsive to receiving a selection of at least one neuropsychiatric condition in the set of neuropsychiatric conditions to form a set of selected neuropsychiatric conditions, generating the set of alternative treatments.

3. The computer implemented method of claim 1 wherein the first set of scans taken at the first time are generated prior to beginning implementation of a therapy in the first set of therapies to treat the patient and wherein the second set of scans taken at the second time are generated a given period of time after beginning implementation of the therapy in the first set of therapies.

4. The computer implemented method of claim 1 wherein the set of neuropsychiatric conditions are identified in a current set of diagnoses, and further comprising:

the physical processor receiving an updated set of diagnoses for the patient, wherein the updated set of diagnoses identifies a different set of neuropsychiatric conditions than the current set of diagnoses;

the physical processor analyzing portions of medical literature associated with the different set of neuropsychiatric conditions to identify a set of recommended treatments for the different set of neuropsychiatric conditions; and the physical processor generating a modified treatment plan using the set of recommended treatments for the different set of neuropsychiatric conditions.

5. The computer implemented method of claim 1 further comprising:

the physical processor identifying a first set of regions of interest in the first set of scans and a second set of regions of interest in the second set of scans;

the physical processor comparing the first set of regions of interest with the second set of regions of interest;

the physical processor identifying a set of changes in the regions of interest occurring over time based on comparing the first set of regions of interest with the second set of regions of interest, wherein the rate of response is determined based on the set of changes;

the physical processor identifying portions of medical literature associated with the set of changes; and the physical processor generating a modified treatment plan, wherein the modified treatment plan comprises a set of links to the portions of medical literature associated with the set of changes in the regions of interest.

6. The computer implemented method of claim 1 further comprising:

the physical processor identifying negative drug interactions, side effects, allergic reactions, and negative effects on pre-existing conditions of the patient associated with a set of alternative treatments for a given neuropsychiatric condition; and the physical processor presenting the modified treatment plan with the negative drug interactions, side effects, allergic reactions, and negative effects on pre-existing conditions of the patient associated with the set of alternative treatments for the given neuropsychiatric condition.

7. The computer implemented method of claim 1 further comprising:

the physical processor generating quantitative information describing a set of changes associated with the neuropsychiatric conditions of the patient occurring over time, wherein the quantitative information comprises data describing structural changes and functional changes associated with regions of interest in the set of scans; and the physical processor comparing the quantitative information with a set of treatment signatures to determine the patient rate of response to the current treatment plan, wherein a treatment signature comprises structural changes and functional changes that are expected to occur during the course of a given treatment.

8. The computer implemented method of claim 1 further comprising:

the physical processor receiving a set of brain scans for a plurality of patients in various demographic groups having an identified neuropsychiatric condition and undergoing a given therapy, wherein the set of brain scans comprises scans taken over a given period of time; and the physical processor analyzing the set of brain scans for the plurality of patients to generate the threshold expected rate of response to the given therapy.

9. The computer implemented method of claim 1 further comprising:

the physical processor analyzing the portions of medical literature and the set of changes to determine a patient rate of response associated with each therapy in the current treatment plan, wherein a given therapy is a therapy to treat a given condition;

the physical processor, responsive to the patient rate of response associated with a given therapy falling below a threshold rate of response for the given therapy, identifying a set of alternative therapies for the given condition; and generating the modified treatment plan using the set of alternative therapies for the given condition.

10. The computer implemented method of claim 1 further comprising:

the physical processor presenting the modified treatment plan with a set of links, wherein the set of links comprises links to portions of medical literature associated with each therapy in the modified treatment plan.

11. A computer program product for modifying treatment plans based on efficacy of treatment, the computer program product comprising:

a computer usable medium having computer usable program code embodied therewith, the computer usable program code comprising:

computer usable program code configured to retrieve a current treatment plan for a patient, wherein the current treatment plan comprises a first set of therapies to treat a set of neuropsychiatric conditions and portions of medical literature associated with the first set of therapies;

computer usable program code configured to analyze a set of scans of the patient to determine a set of changes over time associated with the set of neuropsychiatric conditions, wherein the set of scans comprises a first set of scans taken at a first time and a second set of scans taken at a second time;

computer usable program code configured to analyze the portions of medical literature associated with the set of neuropsychiatric conditions and the set of changes associated with the neuropsychiatric conditions to determine a patient rate of response to the current treatment plan;

computer usable program code configured to identify a set of alternative treatments for the patient in response to the patient rate of response to the current treatment plan falling below a threshold expected rate; and computer usable program code configured to generate a modified treatment plan using the set of alternative treatments.

12. The computer program product of claim 11 further comprising:

computer usable program code configured to present a result of analyzing the portions of medical literature associated with the set of neuropsychiatric conditions, the set of changes associated with the neuropsychiatric conditions, and the treatments in the current treatment plan to a user, wherein the result comprises the current treatment plan and a patient rate of response associated with each neuropsychiatric condition in the set of neuropsychiatric conditions; and computer usable program code configured to generate the set of alternative treatments in response to receiving a selection of at least one neuropsychiatric condition from the set of neuropsychiatric conditions to form a subset of selected neuropsychiatric conditions.

13. The computer program product of claim 11 wherein the first set of scans taken at the first time are generated prior to beginning implementation of a therapy in the first set of therapies to treat the patient and wherein the second set of scans taken at the second time are generated a given period of time after beginning implementation of the therapy in the first set of therapies.

14. The computer program product of claim 11 wherein the set of neuropsychiatric conditions associated with the patient are identified in a current set of diagnoses, and further comprising:

computer usable program code configured to receive an updated set of diagnoses for the patient, wherein the updated set of diagnoses identifies a different set of neuropsychiatric conditions than the current set of diagnoses;

computer usable program code configured to analyze portions of medical literature associated with the different set of neuropsychiatric conditions to identify a set of recommended treatments for the different set of neuropsychiatric conditions; and computer usable program code configured to generate the modified treatment plan using the set of recommended treatments for the different set of neuropsychiatric conditions.

15. The computer program product of claim 11 further comprising:

computer usable program code configured to identify a first set of regions of interest in the first set of scans and a second set of regions of interest in the second set of scans;

computer usable program code configured to compare the first set of regions of interest with the second set of regions of interest;

computer usable program code configured to identify a set of changes in the regions of interest occurring over time based on comparing the first set of regions of interest with the second set of regions of interest, wherein the patient rate of response is determined based on the set of changes;

computer usable program code configured to identify portions of medical literature associated with the set of changes; and computer usable program code configured to generate the modified treatment plan, wherein the modified treatment plan comprises a set of links to the portions of medical literature associated with the set of changes in the regions of interest.

16. The computer program product of claim 11 further comprising:

computer usable program code configured to identify negative drug interactions, side effects, allergic reactions, and negative effects on pre-existing conditions of the patient associated with a set of alternative treatments for a given neuropsychiatric condition; and computer usable program code configured to present the modified treatment plan with the negative drug interactions, side effects, allergic reactions, and negative effects on pre-existing conditions of the patient associated with the set of alternative treatments for the given neuropsychiatric condition.

17. An apparatus comprising:

a bus system;

a communications system coupled to the bus system;

a memory connected to the bus system, wherein the memory includes computer usable program code; and a processing unit coupled to the bus system, wherein the processing unit executes the computer usable program code to retrieve a current treatment plan for a patient, wherein the current treatment plan comprises a first set of therapies to treat a set of neuropsychiatric conditions and portions of medical literature associated with the first set of therapies; analyze a set of brain scans of the patient to determine a set of changes over time associated with the set of neuropsychiatric conditions, wherein the set of scans comprises a first set of scans taken at a first time and a second set of scans taken at a second time; analyze the portions of medical literature associated with the set of neuropsychiatric conditions and the set of changes associated with the neuropsychiatric conditions to determine a patient rate of response to the current treatment plan; identify a set of alternative treatments for the patient in response to the patient rate of response to the current treatment plan falling below a threshold expected rate; and generate a modified treatment plan using the set of alternative treatments.

18. The apparatus of claim 17 wherein the processing unit further executes the computer usable program code to present a result of analyzing the portions of medical literature associated with the set of neuropsychiatric conditions, the set of changes associated with the neuropsychiatric conditions, and the treatments in the current treatment plan to a user, wherein the result comprises the current treatment plan and a patient rate of response associated with each neuropsychiatric condition in the set of neuropsychiatric conditions; and generate the set of alternative treatments in response to receiving a selection of at least one neuropsychiatric condition from the set of neuropsychiatric conditions to form a subset of selected neuropsychiatric conditions.

19. The apparatus of claim 17 wherein the first set of scans taken at the first time are generated prior to beginning implementation of a therapy in the first set of therapies to treat the patient and wherein the second set of scans taken at the second time are generated a given period of time after beginning implementation of the therapy in the first set of therapies.

20. The apparatus of claim 17 wherein the processing unit further executes the computer usable program code to receive an updated set of diagnoses for the patient, wherein the updated set of diagnoses identifies a different set of neuropsychiatric conditions; analyze portions of medical literature associated with the different set of neuropsychiatric conditions to identify a set of recommended treatments for the different set of neuropsychiatric conditions; and generate the modified treatment plan using the set of recommended treatments for the different set of neuropsychiatric conditions.

21. The apparatus of claim 17 wherein the processing unit further executes the computer usable program code to present the modified treatment plan with a set of links, wherein the set of links comprise links to portions of medical literature associated with each therapy in the modified treatment plan.

22. A data processing system for modifying treatment plans based on efficacy of treatment, the system comprising:
a data storage device, wherein the data storage device stores a current treatment plan for a patient, wherein the current treatment plan comprises a first set of therapies to treat a set of neuropsychiatric conditions and portions of medical literature associated with the set of neuropsychiatric conditions;
a set of electronic medical literature sources, wherein the set of electronic medical literature sources comprises medical literature in an electronic form; and
a treatment plan generator, wherein the treatment plan generator analyzes a set of scans of the patient to determine a set of changes over time associated with the set of neuropsychiatric conditions, wherein the set of scans comprises a first set of scans taken at a first time and a second set of scans taken at a second time; analyzes the portions of the medical literature associated with the set of neuropsychiatric conditions and the set of changes associated with the neuropsychiatric conditions to determine a patient rate of response to the current treatment plan; identify a set of alternative treatments for the patient in response to the patient rate of response to the current treatment plan falling below a threshold expected rate; and generate a modified treatment plan, wherein the modified treatment plan comprises the set of alternative treatments.

23. The data processing system of claim 22 wherein the first set of scans taken at the first time are generated prior to beginning implementation of a therapy in the first set of therapies to treat the patient and wherein the second set of scans taken at the second time are generated a given period of time after beginning implementation of the therapy in the first set of therapies.

24. The data processing system of claim 22 further comprising:
a neuroimage analyzer, wherein the neuroimage analyzer analyzes the set of scans to identify a first set of regions of interest in the first set of scans and a second set of regions of interest in the second set of scans, wherein a region of interest is an area that shows an indicator of a neuropsychiatric condition.

25. The data processing system of claim 24 further comprising:
a diagnostic engine, wherein the diagnostic engine generates an updated set of diagnoses based on an analysis of indicators identified in the set of regions of interest and the portions of medical literature associated with the set of neuropsychiatric conditions.

* * * * *